(12) United States Patent
Ehrnsperger et al.

(10) Patent No.: US 10,893,984 B2
(45) Date of Patent: Jan. 19, 2021

(54) ABSORBENT ARTICLES FORMING A THREE-DIMENSIONAL BASIN

(71) Applicant: The Procter & Gamble Company, Cincinnati, OH (US)

(72) Inventors: Bruno Johannes Ehrnsperger, Bad Soden (DE); Hans Adolf Jackels, Mechernich (DE); Claus Peter Stoelzel, Sr., Bad Soden (DE); Christine Elisabeth Zipf, Lauda-Königshofen (DE)

(73) Assignee: The Procter & Gamble Company, Cincinnati, OH (US)

( * ) Notice: Subject to any disclaimer, the term of this patent is extended or adjusted under 35 U.S.C. 154(b) by 982 days.

(21) Appl. No.: 15/044,138

(22) Filed: Feb. 16, 2016

(65) Prior Publication Data
US 2016/0235594 A1 Aug. 18, 2016

(30) Foreign Application Priority Data
Feb. 17, 2015 (EP) .................................... 15155432

(51) Int. Cl.
*A61F 13/49* (2006.01)
*A61F 13/53* (2006.01)
(Continued)

(52) U.S. Cl.
CPC ...... *A61F 13/49001* (2013.01); *A61F 13/494* (2013.01); *A61F 13/49017* (2013.01);
(Continued)

(58) Field of Classification Search
CPC ........ A61F 13/49001; A61F 2013/5326; A61F 13/533; A61F 13/4946; A61F 2013/49493;
(Continued)

(56) References Cited

U.S. PATENT DOCUMENTS 3,744,494 A 7/1973 Marsan
3,860,003 A 1/1975 Buell
(Continued)

FOREIGN PATENT DOCUMENTS

EP 149880 7/1985
EP 0241041 10/1987
(Continued)

OTHER PUBLICATIONS

All Office Actions, U.S. Appl. No. 15/044,146.
(Continued)

*Primary Examiner* — Kathryn E Ditmer
(74) *Attorney, Agent, or Firm* — Wednesday G. Shipp

(57) ABSTRACT

An absorbent article such as a diaper comprises a topsheet, a backsheet and an absorbent core. The absorbent layer comprises at least a longitudinally-extending central portion, and a first and second side portions disposed transversally outward of the central portion. The absorbent core further comprises first and second folding guides between the central portion and the side portions. Each side portion comprises a plurality of winglets, each winglet having a proximal side relative to a folding guide and extending outward from this proximal side, and wherein neighboring winglets are separated by a gap between their neighboring sides. The central portion and the side portions form a three-dimensional basin when the absorbent core is folded along the folding guides. The article further may comprise at least one liquid management layer substantially free of superabsorbent polymer between the topsheet and the absorbent core. The absorbent core may be substantially free of cellulose fibers.

16 Claims, 14 Drawing Sheets

(51) Int. Cl.
*A61F 13/494* (2006.01)
*A61F 13/532* (2006.01)
*A61F 13/537* (2006.01)
*A61F 13/56* (2006.01)
*A61F 13/58* (2006.01)
*A61F 13/45* (2006.01)

(52) U.S. Cl.
CPC ............ *A61F 13/53* (2013.01); *A61F 13/537* (2013.01); *A61F 13/5323* (2013.01); *A61F 13/581* (2013.01); *A61F 2013/4581* (2013.01); *A61F 2013/4948* (2013.01); *A61F 2013/53782* (2013.01); *A61F 2013/53786* (2013.01); *A61F 2013/530883* (2013.01); *A61F 2013/5666* (2013.01)

(58) Field of Classification Search
CPC .............. A61F 13/539; A61F 13/53752; A61F 2013/53765; A61F 2013/53778; A61F 2013/53786
See application file for complete search history.

(56) References Cited

U.S. PATENT DOCUMENTS

| | | | |
|---|---|---|---|
| 3,929,135 A | | 12/1975 | Thompson |
| 4,324,246 A | | 4/1982 | Mullane et al. |
| 4,342,314 A | | 8/1982 | Radel et al. |
| 4,463,045 A | | 7/1984 | Ahr et al. |
| 4,609,518 A | | 9/1986 | Curro et al. |
| 4,629,643 A | | 12/1986 | Curro et al. |
| 4,695,278 A | | 9/1987 | Lawson |
| 4,762,521 A | * | 8/1988 | Roessler ................ A61L 15/60 604/385.26 |
| 4,795,454 A | | 1/1989 | Dragoo |
| 4,808,178 A | | 2/1989 | Aziz et al. |
| 4,909,803 A | | 3/1990 | Aziz et al. |
| 5,006,394 A | | 4/1991 | Baird |
| 5,137,537 A | | 8/1992 | Herron et al. |
| 5,221,274 A | | 6/1993 | Buell et al. |
| 5,554,145 A | | 9/1996 | Roe et al. |
| 5,569,234 A | | 10/1996 | Buell et al. |
| 5,580,411 A | | 12/1996 | Nease et al. |
| 5,607,760 A | | 3/1997 | Roe |
| 5,609,587 A | | 3/1997 | Roe |
| 5,643,588 A | | 7/1997 | Roe et al. |
| 5,700,254 A | | 12/1997 | McDowall et al. |
| 5,792,130 A | | 8/1998 | Widlund et al. |
| 5,968,025 A | | 10/1999 | Roe et al. |
| 5,971,153 A | * | 10/1999 | Bauer .................. A61F 13/5511 206/494 |
| 6,004,306 A | | 12/1999 | Robles et al. |
| 6,328,724 B1 | | 12/2001 | Ronnberg et al. |
| 6,420,627 B1 | | 7/2002 | Ohnishi et al. |
| 6,520,945 B1 | | 2/2003 | Hansson |
| 6,632,504 B1 | | 10/2003 | Gillespie et al. |
| 6,645,569 B2 | | 11/2003 | Cramer et al. |
| 6,689,933 B1 | | 2/2004 | DiPalma |
| 6,716,441 B1 | | 4/2004 | Roe et al. |
| 6,863,933 B2 | | 3/2005 | Cramer et al. |
| 7,112,621 B2 | | 9/2006 | Rohrbaugh et al. |
| 7,169,136 B2 | | 1/2007 | Otsubo et al. |
| 7,220,251 B2 | * | 5/2007 | Otsubo ............ A61F 13/49001 604/385.201 |
| 7,329,246 B2 | | 2/2008 | Kinoshita et al. |
| 7,588,561 B2 | | 9/2009 | Kenmochi et al. |
| 7,732,039 B2 | | 6/2010 | Chavravarty et al. |
| 7,744,576 B2 | | 6/2010 | Busam et al. |
| 9,789,009 B2 | | 10/2017 | Joseph |
| 10,137,040 B2 | * | 11/2018 | Ehrnsperger ............ A61F 13/53 |
| 10,456,305 B2 | | 10/2019 | Ehrnsperger et al. |
| 2001/0056271 A1 | | 12/2001 | Shingu |
| 2002/0028858 A1 | | 3/2002 | Diehl et al. |
| 2002/0087140 A1 | | 7/2002 | Otsubo |
| 2002/0151861 A1 | | 10/2002 | Klemp et al. |
| 2003/0105190 A1 | | 6/2003 | Diehl et al. |
| 2003/0148684 A1 | | 8/2003 | Cramer et al. |
| 2004/0068244 A1 | | 4/2004 | Salone |
| 2004/0243078 A1 | * | 12/2004 | Guidotti ................ A61F 13/537 604/367 |
| 2005/0008839 A1 | | 1/2005 | Cramer et al. |
| 2005/0033252 A1 | | 2/2005 | Schneider et al. |
| 2005/0033253 A1 | | 2/2005 | Fuchs et al. |
| 2005/0043694 A1 | | 2/2005 | Schneider et al. |
| 2005/0143711 A1 | | 6/2005 | Otsubo |
| 2005/0148970 A1 | | 7/2005 | Kudo et al. |
| 2006/0004334 A1 | * | 1/2006 | Schlinz ................ A61F 13/534 604/366 |
| 2006/0024433 A1 | | 2/2006 | Blessing et al. |
| 2006/0040579 A1 | * | 2/2006 | Sheldon .................. A61F 13/53 442/366 |
| 2006/0184146 A1 | * | 8/2006 | Suzuki .................. A61F 13/535 604/358 |
| 2007/0244455 A1 | * | 10/2007 | Hansson ............ A61F 13/4704 604/385.201 |
| 2008/0119810 A1 | | 5/2008 | Kuroda et al. |
| 2008/0312617 A1 | | 12/2008 | Hundorf et al. |
| 2008/0312622 A1 | | 12/2008 | Hundorf et al. |
| 2008/0312624 A1 | | 12/2008 | Hundorf et al. |
| 2008/0312625 A1 | | 12/2008 | Hundorf et al. |
| 2008/0312627 A1 | | 12/2008 | Takeuchi et al. |
| 2009/0112175 A1 | | 4/2009 | Bissah |
| 2010/0051166 A1 | | 3/2010 | Hundorf et al. |
| 2011/0073513 A1 | | 3/2011 | Weisman et al. |
| 2011/0152813 A1 | | 6/2011 | Ellingson |
| 2011/0184364 A1 | | 7/2011 | Biggs et al. |
| 2011/0250413 A1 | | 10/2011 | Lu et al. |
| 2011/0268932 A1 | | 11/2011 | Catalan et al. |
| 2011/0319848 A1 | | 12/2011 | McKiernan et al. |
| 2012/0312491 A1 | | 12/2012 | Jackels et al. |
| 2012/0316526 A1 | | 12/2012 | Rosati et al. |
| 2012/0316528 A1 | * | 12/2012 | Kreuzer ................ A61F 13/533 604/366 |
| 2013/0090620 A1 | | 4/2013 | Carbonari |
| 2014/0027066 A1 | | 1/2014 | Jackels et al. |
| 2014/0163506 A1 | | 6/2014 | Roe et al. |
| 2015/0173968 A1 | | 6/2015 | Joseph |
| 2016/0113825 A1 | | 4/2016 | Bianchi et al. |
| 2016/0175168 A1 | | 6/2016 | Zink, II |
| 2016/0235595 A1 | | 8/2016 | Ehrnsperger et al. |
| 2016/0235596 A1 | * | 8/2016 | Ehrnsperger .......... A61F 13/532 |
| 2016/0235597 A1 | * | 8/2016 | Ehrnsperger ...... A61F 13/49001 |
| 2016/0235602 A1 | * | 8/2016 | Ehrnsperger ............ A61F 13/53 |
| 2016/0235603 A1 | * | 8/2016 | Ehrnsperger .......... A61F 13/532 |
| 2016/0235604 A1 | | 8/2016 | Ehrnsperger |
| 2016/0235605 A1 | * | 8/2016 | Ehrnsperger ............ A61F 13/53 |
| 2020/0000647 A1 | | 1/2020 | Ehrnsperger |

FOREIGN PATENT DOCUMENTS

| | | | | |
|---|---|---|---|---|
| EP | 2813201 | | 12/2014 | |
| JP | 2013-000238 A | | 1/2013 | |
| JP | 2013000238 | * | 1/2013 | ............ A61F 13/49 |
| WO | WO 95/10996 | | 4/1995 | |
| WO | WO 95/16418 | | 6/1995 | |
| WO | WO 95/24173 | | 9/1995 | |
| WO | WO 97/33815 | | 9/1997 | |
| WO | WO 9822279 | * | 5/1998 | ............ D04H 13/00 |
| WO | WO 00/45762 | | 8/2000 | |
| WO | WO 2000/59430 | | 10/2000 | |
| WO | WO 02/067809 | | 9/2002 | |
| WO | WO 03/105738 | | 12/2003 | |
| WO | WO 2005/105010 | | 11/2005 | |
| WO | WO 2006/059922 | | 6/2006 | |
| WO | WO 2006/068549 | | 6/2006 | |
| WO | WO 2007/069958 | | 6/2007 | |
| WO | WO 2008/155702 | | 12/2008 | |
| WO | WO 2008/155722 | | 12/2008 | |
| WO | WO 2011/041352 | | 4/2011 | |
| WO | WO 2011/163582 | | 12/2011 | |
| WO | WO 2012/074466 | | 6/2012 | |
| WO | WO 2012/170341 | | 12/2012 | |

(56) References Cited

FOREIGN PATENT DOCUMENTS

| WO | WO 2012/170778 | 12/2012 |
| --- | --- | --- |
| WO | WO 2012/174026 | 12/2012 |
| WO | WO 2014/078247 | 5/2014 |
| WO | WO 2014/093310 | 6/2014 |
| WO | WO 2014/093323 | 6/2014 |
| WO | WO 2015/031229 | 3/2015 |

OTHER PUBLICATIONS

All Office Actions, U.S. Appl. No. 15/044,164.
All Office Actions, U.S. Appl. No. 15/044,173.
All Office Actions, U.S. Appl. No. 15/044,183.
All Office Actions, U.S. Appl. No. 16/568,634.
Dictionary.com "To", available at https://www.dictionary.com/browse/to, accessed Oct. 15, 2018.

* cited by examiner

ABSORBENT ARTICLES FORMING A THREE-DIMENSIONAL BASIN

FIELD OF THE INVENTION

The invention relates to personal hygiene absorbent articles of the type worn in the crotch region of a wearer to absorb body exudates, in particular but not limited to baby diapers and adult incontinence products.

BACKGROUND OF THE INVENTION

Modern diapers typically comprise an absorbent core containing a mixture of cellulose fibers and superabsorbent polymer ("SAP") particles as absorbent material. Over the years, the relative amount of SAP in the absorbent core has increased thus providing thinner absorbent cores. Absorbent articles with an absorbent core material without cellulose fibers, so called airfelt-free cores, have also been recently proposed. Absorbent cores comprising a central portion and two side portions separated by folding guides have also been suggested for providing an improved fit and reduced leakage.

Typically, as absorbent articles become saturated with urine, they tend to sag down in the crotch region of the wearer due to the weight of the fluid. This may cause loss of contact of the article along the thighs of the wearer and increase the possibility of leakages. While elastic waist bands and other elasticized parts such as barrier leg cuffs are commonly used to maintain contact and fit, these solutions are limited and leakage can still occur, especially if the diaper was not put in place correctly or was displaced out of position by the wearer.

Despite the improvements suggested in the prior art, there is a continuous need for improving dry and wet fit, wearing comfort, and fluid handling properties, including fluid acquisition and reduced leakage, of absorbent articles while keeping the cost of production as low as possible. Furthermore, there is a need for articles that are easy to apply symmetrically on the wearer and conform to the shape of the body. The present invention addresses these multiple requirements.

SUMMARY OF THE INVENTION

The invention is directed to an absorbent article comprising a topsheet on the wearer-facing side, a backsheet on the garment-facing side and an absorbent core between the topsheet and the backsheet. The absorbent core comprises an absorbent layer having a longitudinally-extending central portion, a first side portion disposed transversally outward of the central portion and a second side portion disposed transversally outward of the central portion on another side of the central portion. The absorbent core further comprises folding guides between the central portion and the first and second side portions.

Each side portion comprises a plurality of winglets having a proximal side relative to a folding guide and that extend outward from this proximal side. Two neighboring winglets are separated from another by a gap between their neighboring sides. At least some of these gaps may be generally triangularly shaped. The central portion and the side portions form a three-dimensional basin when the absorbent core is folded along the folding guides. In this basin configuration, the gaps between the neighboring winglets decrease and optionally entirely close to form the side walls of the basin. The rest of the article, in particular the backsheet, topsheet and the barrier leg cuffs and gasketing cuffs when present, can follow the basin configuration of the absorbent core. The absorbent article may advantageously comprise at least one elasticized element that helps the absorbent core and article to spontaneously fold along the folding guides and thus form the basin shape when the article is placed on the wearer.

In a first aspect, the article may further comprise at least one liquid management layer between the topsheet and the absorbent core. In another aspect, the absorbent core may be substantially free of cellulose fibers. In another aspect the core wrap may be attached through the folding guides and/or through the gaps between neighboring winglets. This and other aspects of the invention that may advantageously be combined are further described in the description below.

BRIEF DESCRIPTION OF THE DRAWINGS

FIG. 8 is a top view of the lower liquid management layer of FIG. 4a;

FIG. 9 is a top view of the upper liquid management layer of FIG. 4a;

DETAILED DESCRIPTION OF THE INVENTION

Introduction

As used herein in the specification and the claims, the term "central portion", "side portion", "folding guide" and "winglets" without further qualification refer to these elements as part of the absorbent core, unless specified otherwise or wherein it is apparent from the context that these terms refer to another layer. When these terms are further qualified by "liquid management layer", as in "liquid management layer's central portion", they refer to these elements as part of the liquid management layer.

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred, advantageous or exemplary embodiments described below are not limiting the scope of the claims, unless specifically indicated to do so. The words "typically", "normally", "preferably", "advantageously", "in particular" and the likes also qualify features which are not intended to limit the scope of the claims, unless specifically indicated to do so. Any feature or component described herein in relation with one embodiment may be combined with another feature or component of another embodiment unless indicated otherwise.

Figure 1:
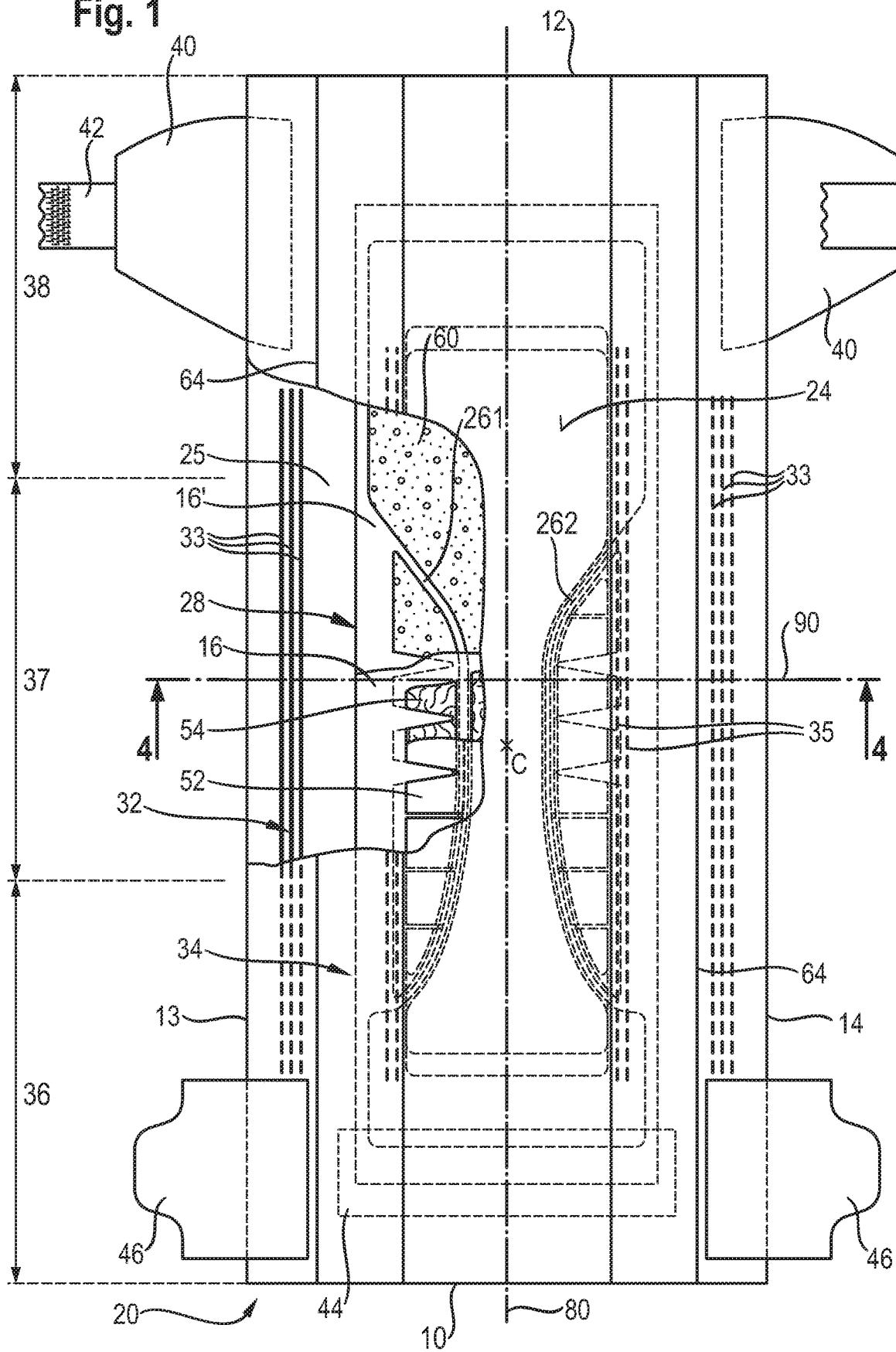
FIG. 1 is a top view of an exemplary article, flattened-out, and with some layers partially removed to better show the inner layers.

Unless indicated otherwise, the description and claims refer to the absorbent article, absorbent core or component thereof before use (i.e. dry, and not loaded with a fluid) and conditioned at least 24 hours at 21° C.+/−2° C. and 50+/−20% Relative Humidity (RH) and in a flat state as shown for example on FIG. 1.

The absorbent articles of the invention and their components will now be discussed generally and with exemplary reference to the Figures and the numerals referred to in these Figures for illustration purpose. These examples are not intended to limit the scope of the claims unless specifically indicated.

General Description of an Absorbent Article 20

An exemplary absorbent article according to the invention is represented in FIG. 1 in the form of a baby taped diaper 20. FIG. 1 is a top plan view of the wearer-facing side of the exemplary diaper, in a flat-out state, with portions of the structure being cut-away to more clearly show the construction of the diaper. This diaper 20 is shown for illustration purpose only, and the invention is not limited to a specific type of personal hygiene absorbent articles. The absorbent article can also be for example a pant-type article with pre-formed side seams. The articles may be intended for babies, toddlers, but also for adult incontinence. The term "absorbent article" refers to a finished product that can be directly used by the user. Unless otherwise indicated, dimensions and areas disclosed herein apply to the article in this flat-out configuration. If some part of the article is under tension due to elasticized components, the article may be typically flattened using clamps along the periphery of the article and/or a sticky surface, so that the topsheet and backsheet can be pulled taut so as to be substantially flat. Closed articles such as training pant may be cut open along the side seams to apply them on a flat surface. Closed belt products not having a side seam can also be cut along the side edges.

The absorbent article 20 comprises a front edge 10, a back edge 12, and two longitudinally-extending side (lateral) edges 13, 14 joining the front edge and the back edge. The front edge 10 is the edge of the article which is intended to be placed towards the front of the user when worn, and the back edge 12 is the opposite edge. The absorbent article is notionally divided by a longitudinal axis 80 extending from the front edge to the back edge of the article and dividing the article in two substantially symmetrical halves relative to this axis, when viewing the article from the wearer facing side in a flat out configuration, as exemplarily shown in FIG. 1. This axis 80 may typically be concomitant with the longitudinal axis 80' of the absorbent core. The absorbent article has a length L as measured along the axis 80 from the back edge to the front edge. The absorbent article can also be notionally divided by a transversal axis 90 into a front region and a back region of equal length measured on the longitudinal axis, when the article is in such a flat state. The article's transversal axis 90 is defined as perpendicular to the longitudinal axis 80 and placed at half the length of the article. The point on the longitudinal axis 80 of the article placed at a distance of 0.45 of L (0.45 L) from the front edge 10 of the article is referred herein as the crotch point "C".

The absorbent article is further notionally divided in a front region 36, a back region 38 and in between a crotch region 37. The front region 36 is defined as the region of the article extending from the front edge 10 and having a length of a third of L along the longitudinal axis 80. The back region 38 is defined as the region of article extending from the back edge 12 of the article and having a length of one third of L along the longitudinal axis 80. The crotch region 37 is the intermediate region between the front and back regions, and also having a length of a third of L along the longitudinal axis 80.

Figure 2:
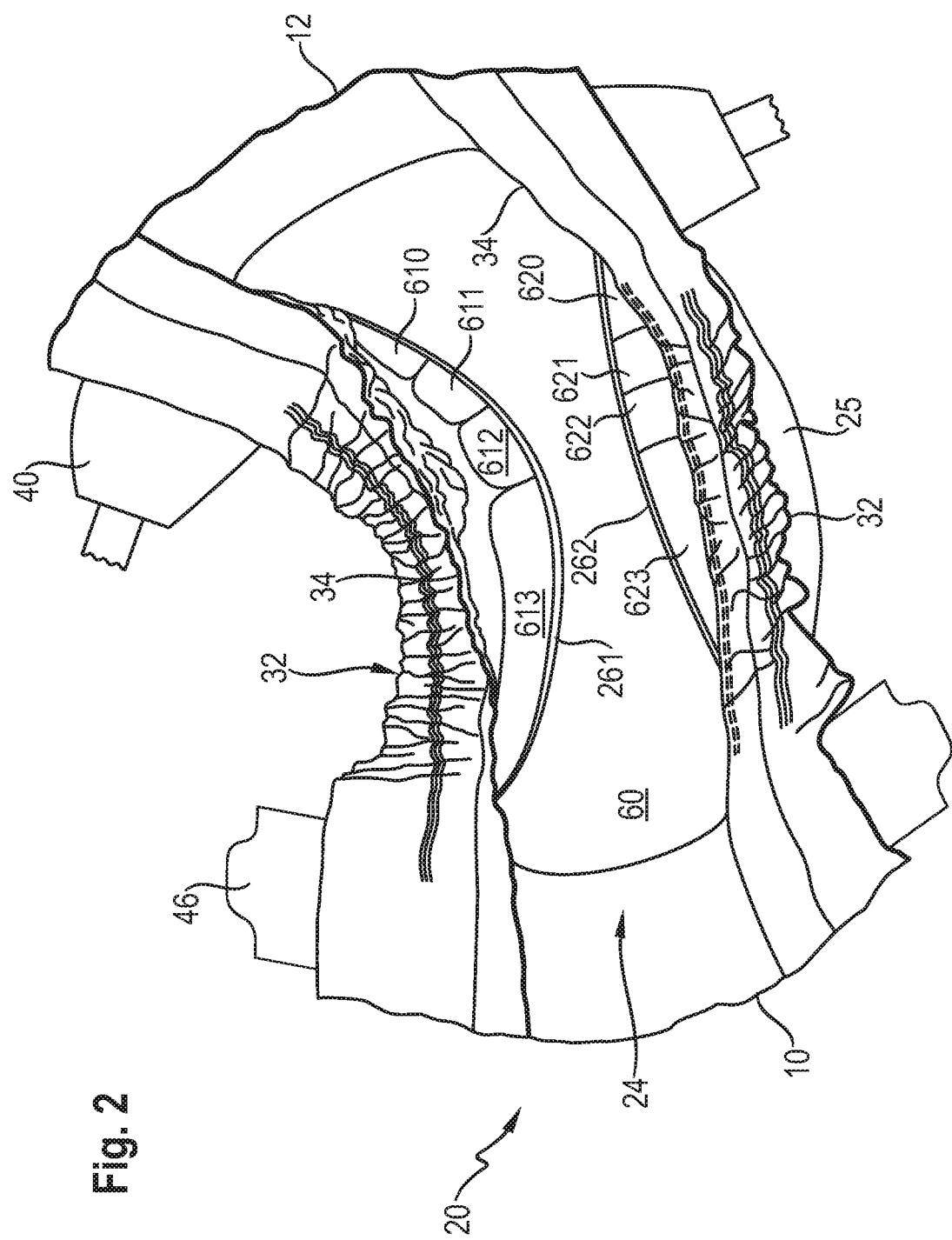
FIG. 2 is a perspective view of the same article in a basin configuration, with the layers above the absorbent layer removed from view.

FIG. 2 shows the same diaper in a folded configuration wherein the absorbent core has taken a basin-shaped configuration with the winglets 610-613, 620-623 forming the side walls of the basin. For a better understanding, the layers above the absorbent layer have been omitted from this drawing. The liquid management layer(s) can follow this basin-shaped three-dimensional configuration when the article is put on the wearer, as will be described further below. Also, other elements of the absorbent article such as the cuff, backsheet and topsheet typically follow and further extend the basin shape of the absorbent core in the folded configuration.

Figure 3:
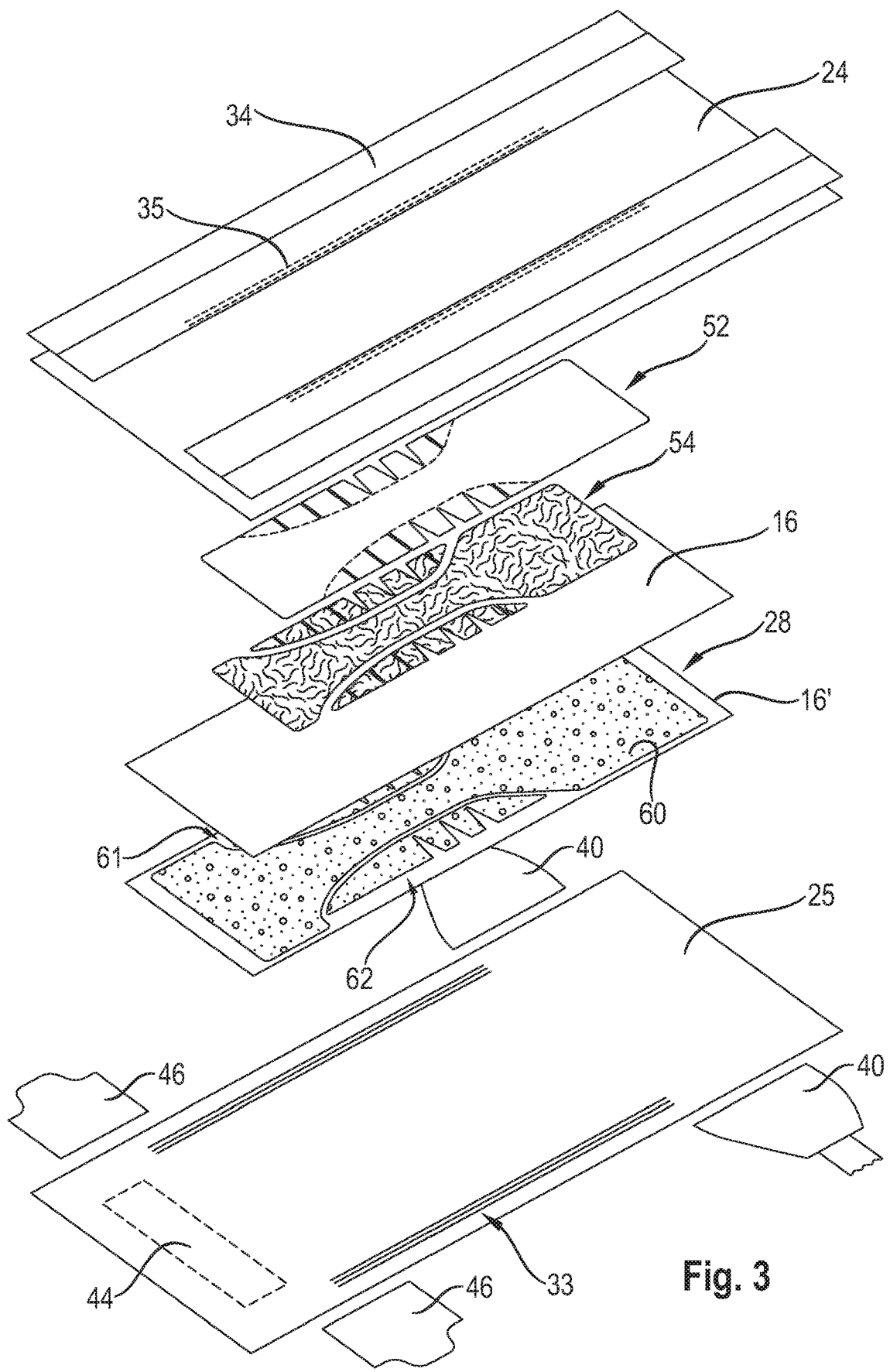
FIG. 3 is an exploded perspective view of several layers of the article of FIG. 1.

FIG. 3 shows some of the layers of the diaper of FIG. 1 in exploded view. The wearer-facing side of the diaper comprises a liquid permeable topsheet 24, the garment-facing surface comprises a liquid impermeable backsheet 25, and an absorbent core 28 is present between the topsheet 24 and the backsheet 25. The article represented comprises two liquid management layers: a liquid acquisition layer 52 and a liquid distribution layer 54. However in many applications a single liquid management layer will be sufficient. The liquid management layers are substantially free of superabsorbent polymer and are at least partially disposed between the topsheet and the absorbent core.

The article may also comprise a pair of barrier leg cuffs 34 each having a free standing edge 66 with an elasticized section 35, as well as gasketing cuffs 32 comprising an elasticized component 33 in the chassis of the diaper. Typical other absorbent article components may also be present, some of which are represented such as the fastening system 40-44 (however not included for pant-type diapers). The topsheet 24, the backsheet 25, the absorbent core 28 and the other article components may be assembled in a variety of well-known configurations, in particular by gluing, fusion and/or pressure bonding. Exemplary diaper assemblies are for example generally described in U.S. Pat. Nos. 3,860,003, 5,221,274, 5,554,145, 5,569,234, 5,580,411, and 6,004,306. The absorbent article may be advantageously thin, in particular for baby care applications, for example with a caliper of from 2.0 mm to 8.0 mm, in particular from 3.0 mm to 6.0 mm, at the crotch point or any other point of the article, as measured using the Thickness Measurement Method described below. The absorbent article's maximal thickness as measured according to the Thickness Measurement Method described herein may in particular advantageously be no more than 8.0 mm, or no more than 6.0 mm.

The different components of the article and how they interact will now be discussed in more details.

Absorbent Core 28

As used herein, the term "absorbent core" refers to a component of an absorbent article comprising an absorbent material layer, which is typically enclosed in a core wrap formed by a top layer and a bottom layer. The absorbent core is typically an individual component which is attached directly or indirectly to other components of the article such as a topsheet and a backsheet to form the article in a converting line. The terms "absorbent core" and "core" are herein used interchangeably. It is however not excluded that the absorbent material layer may be directly deposited on one or more layer(s) such as the liquid management layer or the backsheet without a separate core wrap, in which case the core wrap may be at least partially formed by one of these layers.

Figure 5:
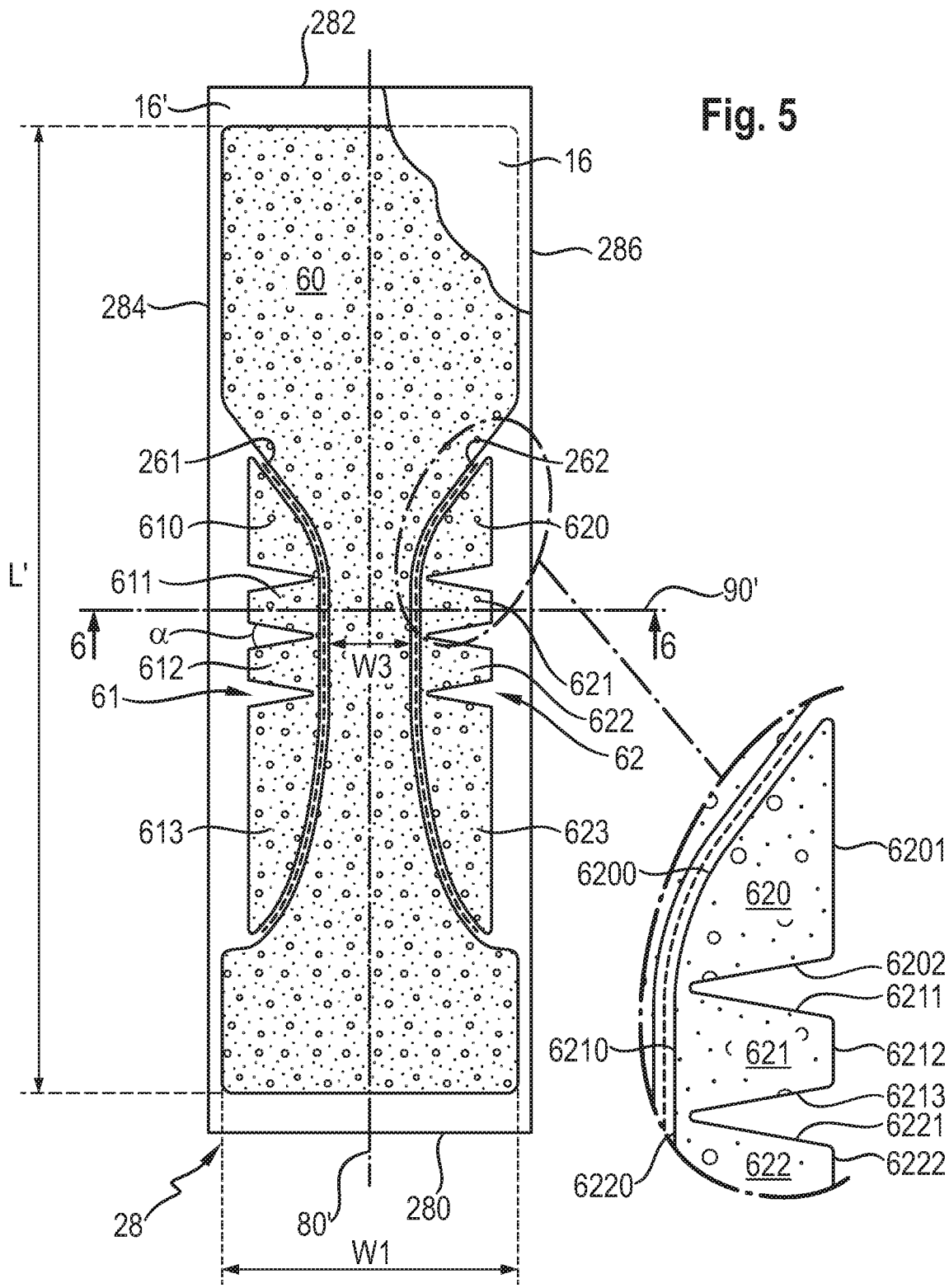
FIG. 5 is a top view of the absorbent core of the article of FIG. 1 taken in isolation.

The absorbent core comprises a layer of absorbent material that comprises a central portion 60, and two side portions 61, 62 disposed transversally outward on opposite sides of the central portion, as illustrated in FIG. 5. A first folding guide 261 and a second folding guide 262 are present between the central portion and the each of the two side portions respectively. The absorbent layer, including each of the central portion and the side portions may be typically symmetrical relative to the longitudinal centerline 80' of the core.

The absorbent material of the invention typically comprises a superabsorbent polymer. Advantageously, the absorbent material may be substantially free of cellulosic fibers, but it is not excluded that the absorbent material comprises higher amount of cellulose fibers, for example up to 50% by weight of the absorbent material in the absorbent core. The core wrap is not considered as absorbent material for the purpose of calculating the percentage of superabsorbent polymer (SAP) in the absorbent core. The absorbent core is typically the component with the most absorbent capacity of all the components of the absorbent article, and which comprises all, or at least the majority of, superabsorbent polymer (SAP). The core may consist essentially of, or consist of, the core wrap, the absorbent material and optionally adhesives. The core wrap can be typically formed by one or two layers of a nonwoven, paper or tissue material with a suitable bonding along its longitudinal sides, and optionally also at its front end and back end, for containing the absorbent material.

The absorbent cores of the invention can be typically laid flat on a planar surface, as exemplarily represented on FIG. 5. The absorbent cores may also be typically thin and conformable, so that they can also be laid on a curved surface for example a drum during the making process, or stored and handled as a continuous roll of stock material before being converted into an absorbent article. Unless otherwise indicated, dimensions and areas disclosed herein apply to the core in this flat-out configuration. The same applies to an absorbent article, as exemplarily represented in FIG. 1 as a taped diaper, in which the core is incorporated.

The absorbent core may be relatively thin relative to its thickness, and principally extend in a transversal direction and a longitudinal direction. These directions typically correspond to the transversal 80 and longitudinal 90 directions respectively of the article in which the core is incorporated. The absorbent core 28 can thus be notionally divided by a longitudinal axis 80' parallel to the longitudinal direction and extending from the front edge 280 to the back edge 282 and dividing the core in two substantially symmetrical halves relative to this axis. Similarly, a transversal axis 90' can be defined as dividing the core in two halves of equal length along the perpendicular direction in the plane formed by the core.

Figure 6:
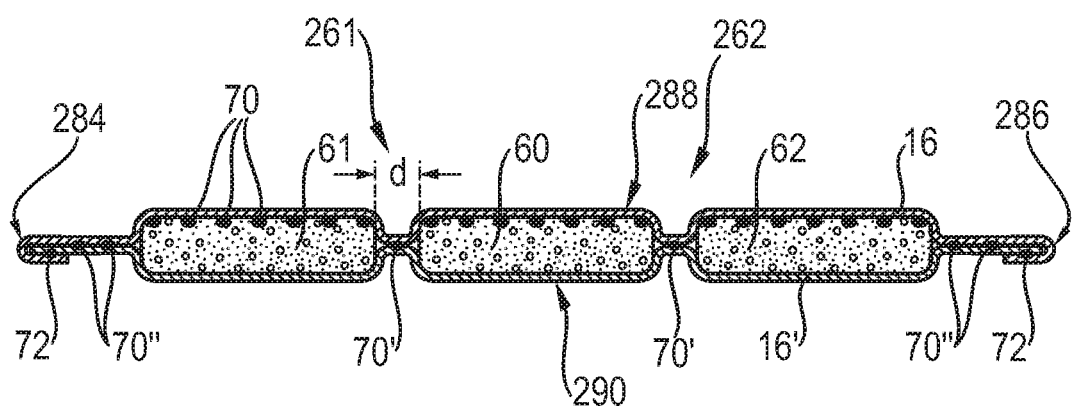
FIG. 6 shows a transversal cross-section of the core of FIG. 5.

The absorbent core 28, as illustrated in FIGS. 5-6, may comprise a front edge 280, a back edge 282 and two longitudinal side edges 284, 286 joining the front edge and the back edge. The front edge of the core is the edge intended to be placed towards the front edge of the absorbent article in which the core is or will be integrated. Typically the front and back edges 280, 282 of the core may be shorter than the longitudinal side edges 284, 286 of the core. The absorbent core also comprises a top side 288 and a bottom side 290. The top side of the core is placed or intended to be placed towards the wearer-facing side (topsheet 24) of the article and the bottom side is the side placed or intended to be placed towards the garment-facing side (backsheet 25) in the finished article.

Core Wrap 16, 16'

The core wrap may, as shown in the cross-sectional view of FIG. 6, comprise a first substrate 16 on the top side 288 of the core (herein also referred to as top layer) and a second substrate 16' on the bottom side 290 of the core (herein also referred to as bottom layer). The top layer may be advantageously more hydrophilic than the bottom layer, for example after treatment with a wetting agent as is known in the art. The top layer may also have smaller pores than the bottom layer in order to avoid absorbent material migrating towards the body-wearer facing side of the article. The bottom layer may be thicker and/or have more loft to avoid pock marking, i.e. to prevent absorbent particles from the core pocking holes into the backsheet. It is however not excluded that the core wrap may be formed for example by a single piece of nonwoven material sealed along its length.

When the core wrap is made of two substrates, a C-wrap seal along each longitudinal side edges 284, 286 of the core may be formed as shown on FIG. 6. In such a C-wrap seal, a flap of the first substrate is folded over the second substrate along each of the longitudinal side edges of the core, and this flap attached on the second substrate, for example using an adhesive or fusion-bond 72, as is known in the art. The front and back edges of the core wrap may be for example bonded flat to each other (so-called "sandwich" bonding). Examples of such core wrap constructions can be found in WO2014/093310. It is also possible to form a core wrap from a single piece of nonwoven material which is folded over the superabsorbent material layer and use a small overlap to the nonwoven to itself in the longitudinal direction. The core wrap may be sealed along its periphery or only along its longitudinal edges or not sealed along any edges. The central portion and the side portions of the absorbent layer may typically not extend to the very edges of the core wrap so that sufficient core wrap material is present to provide for such seals.

The core wrap substrate may be any material suitable for receiving and containing the absorbent material. Typical substrates are in particular nonwovens, paper, tissues, films, wovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 and US2011/0250413A1. Nonwoven materials provided from synthetic fibers may be used, such as PE, PET and in particular PP. The overall shape of the core wrap may be rectangular, as seen on FIG. 5, as may be relatively easily produced by unwinding the core wrap material(s) from one or two rolls with fixed width and cutting and optionally folding the wrap material to form the edges 280, 282, 284, 286 of the core. Other shapes for the periphery of the core wrap are also possible, for example following generally the shape of the absorbent layer.

As represented in FIG. 6 by the bond 70', the top layer 16 of the core wrap may be advantageously bonded to the bottom layer 16' through the folding guide areas, for example by using an adhesive bond, a mechanical bond, a fusion bond, an ultrasonic bond or any combinations of these. The folding guides may thus be advantageously areas of the core which are substantially free of absorbent material to facilitate making these bonds. By "substantially free" it is meant that accidental contamination by some absorbent material such as SAP particles during the making process is not excluded. These bonds can help preventing that the absorbent material fills the areas of the folding guides prematurely, before use or during use (when the absorbent material swells). Such bonding between the top layer and the lower layer of the core wrap has been disclosed for example in WO2012/170,778 (Rosati). The core wrap may also be bonded in other areas, for example in areas formed by the gaps between the winglets, or between the side portion and the longitudinal side edges of the core. Such bonds 70" may be for example formed by an adhesive bond, a mechanical bond, a fusion bond, an ultrasonic bond or any combinations of these. Although other type of bonds may be used, an auxiliary glue 70 may be applied to the side of the top layer and/or the bottom layer facing the absorbent layer across the width of the absorbent core, for example by slot-coating as is known in the art and as will discussed further below, to form these bonds 70', 70". This may help immobilizing the absorbent material according to the desired pattern. C-wrap seals 72 may also be formed along the longitudinally-extending side edges of the core, as shown on FIG. 6, for example by slot-coating a glue. These bonds 70', 70", except for the C-wrap bonding 72, may be designed to open when the absorbent core reaches a certain amount of saturation, to release more space where the absorbent material can expand.

Absorbent Layer's Central Portion 60

As illustrated on FIG. 5, the central portion 60 comprises a front edge, adjacent the front edge 280 of the core, a back edge adjacent the back edge 282 of the core and two longitudinal edges connecting the front and back edges. The central portion has a length L' measured along the longitudinal axis 80'. The central portion 60 is advantageously shaped, or in other words non-rectangular, although a rectangular shape for the central portion is not excluded. The central portion may have a maximum width W1 for example towards its front edge and/or its back edge, and a minimum width W3 in an intermediate position, as measured along the transversal direction 90'.

The longitudinal edges of the central portion may form a first recess and a second recess respectively, in particular in an intermediate position between the front edge and the back edge of the central portion. The overall shape of the central portion may thus be a dog-bone or a hour-glass shape when seen from the above, as illustrated in FIG. 5. The central portion may have a minimum width W3 at an intermediate longitudinal position between the front edge and back edge of the central portion. The minimum width W3 of the central portion may for example range from 10% to 80% of the maximum width W1 of the central portion, in particular from 15% to 70% of W1, in particular from 20% to 60% of W1, for example 40%. The central portion may have, as represented, a constant width in the areas outside the recesses, but other configurations are possible, for example the width may continuously expand towards the front and/or back edges of the core. Although the front edge and the back edge of the central portion may be substantially straight, it is not excluded that these may be curved, concave or convex, or one convex and the other concave.

The central portion may be unitary, as represented, but it is not excluded that it comprises sub-sections, for example separated by further transversally-orientated folding guides to provide more flexibility in the longitudinal direction. The amount of absorbent material in the central portion may be typically profiled, so that a higher basis weight of absorbent material is disposed towards the middle of the central portion, in particular between the side portions, and towards the front edge of the central portion, relative to the back edge of the central portion.

Absorbent Layer's Side Portions 61, 62

The first side portion 61 and the second side portion 62 of the absorbent layer may be typically at least partially disposed within the areas defined by the recesses formed by the intermediate tapering of the central portion 60. The side portions may expand transversally outward further than the central portion, however this may require additional core wrap material on the longitudinal side to cover the overhanging side portions. Thus it may be advantageous that the side portions are entirely encompassed within the recesses formed by the central portion so as to eliminate or reduce the need for additional core wrap material on the longitudinal sides of the core. The outward-most positions of the side portions may thus be flush with, or inwards of, the longitudinally-extending side edges of the central portion at their largest width. The first and second side portions may typically be symmetrical to each other relative to the longitudinal axis 80' of the core.

Winglets (610-613, 620-623)

Figure 11:
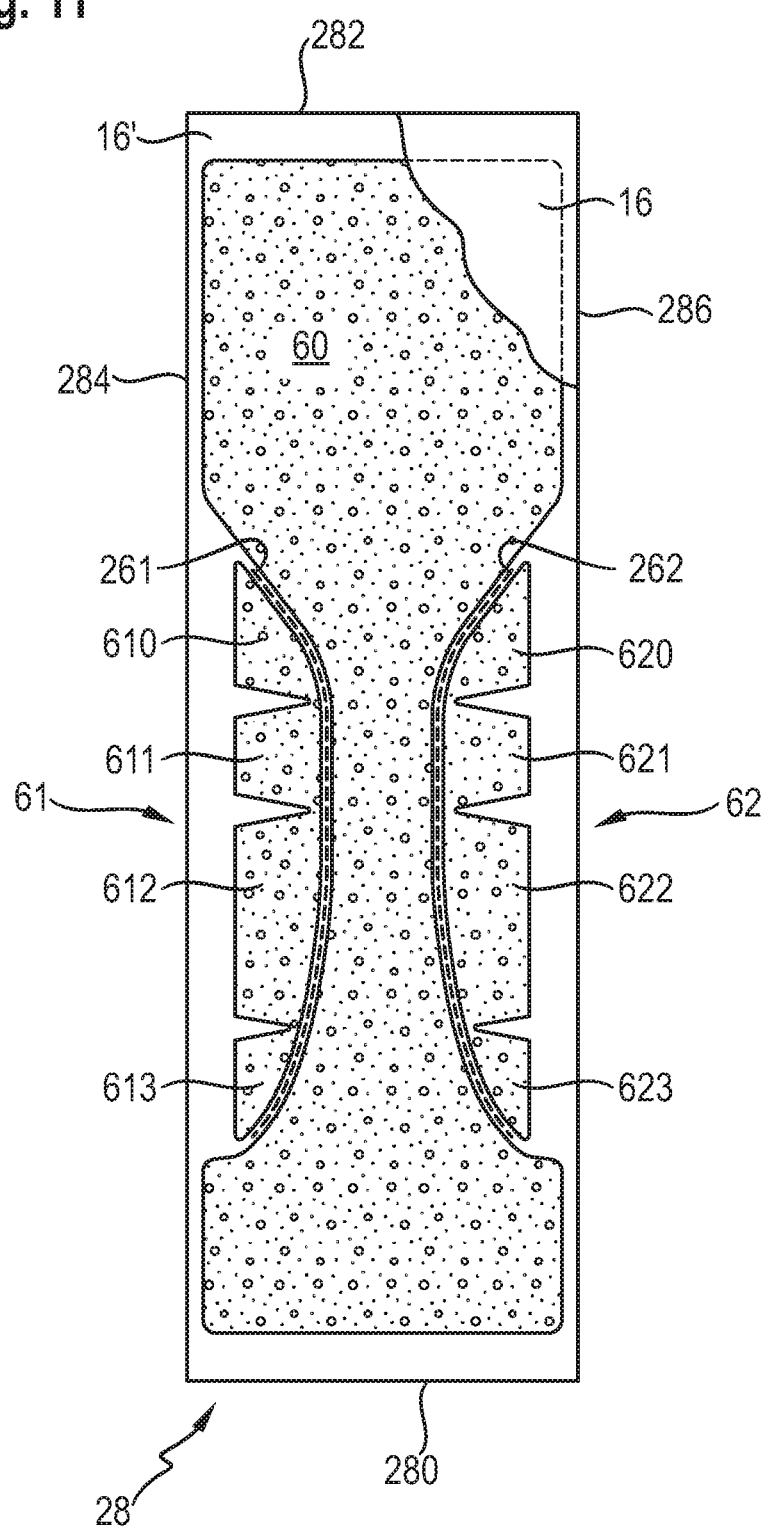
FIG. 11 is a top view of an alternative absorbent core.

The side portions 61, 62 each comprises a plurality of neighboring winglets 610-613, 620-623. The winglets may also be described as flaps, and typically have a small size relative to the area of the central portion. FIG. 5 shows a close-up view of some of the winglets on the second side portion 62. Each winglet is defined by a proximal side 6200, 6210, 6220, 6230 . . . which is closest to a folding guide and from which the winglet extend outward, and at least two and typically three further sides. The proximal side of each winglet may be directly adjacent, i.e. less than 10 mm away from the centerline of the closest folding guide. Each winglet may be completely separated from the neighboring winglets, but it is not excluded that some or all of the winglets are linked to each other by a continuous absorbent material area proximal to the folding guide. An alternative arrangement for the winglets is shown in FIG. 11.

Within each side portion, the winglets are generally aligned next to another, with their neighboring sides 6202-6211, 6213-6221, 6223-6231 . . . separated by a gap as illustrated on FIG. 5. At least one of the gaps on each side portion may be generally triangular or in other word wedge-shaped, when the article and core is shown in a flattened-out state as shown on FIG. 5. For these triangular gaps, the width of the gaps increases with the distance from the proximal sides of the winglets. The angle α (alpha) formed by the neighboring sides of two neighboring winglets at their proximal sides may for example range of from about 5° to about 60°, in particular 10° to about 50°, for example 30°.

Typically, the higher the angle, the higher the radius of curvature can be achieved in the basin configuration. This angle may be the same or different for each gap.

In addition to the generally triangular gaps, at least one of the gaps (not represented) on each side portion may be have substantially constant width. These gaps may be in particular generally straight, in particular be parallel to the transversal axis as illustrated in the Figures, but it is also possible that they are straight and angled relative to the transversal axis, or not straight but curved. The width of such gaps gap may in particular range of from 1 mm to 8 mm, more precisely from 2 mm to 6 mm, but other values are possible. These constant width gaps may or may not decrease when the absorbent core comes into the basin configuration. Rather, they provide for increase flexibility of the side portions which may be useful needed when the absorbent article is put on the wearer and the core takes its basin shape when the article is worn on the user.

The winglets in each side portion may all have the same shape, but advantageously they will have different shapes that are in particular adapted to the curvature of the closet folding guides. The winglets may in particular be generally triangular, especially for the first and last winglets of a side portion (as winglets 610, 620, 613, 623 in FIG. 5) and generally quadrilateral for the intermediate winglets 611, 621, 612, 622. Various quadrilateral shapes are possible, in particular the winglets may be generally trapezoidal (quadrilateral with at least two sides parallel). The word "generally" as used herein means that the corners and sides of the winglets are not necessarily geometrically exactly forming the shape indicated, but the corners may be slightly rounded and the sides not delimited by perfect straight lines. As represented in the close-up view on FIG. 5, some or all of the winglets may have a distal edge 6201, 6212, 6222 parallel to the longitudinal side edge 284, 286 of the core.

When the absorbent core is folded along the folding guides to form the three-dimensional basin, the gaps between the neighboring sides of the winglets decrease, in other words the neighboring sides become closer to another, and may optionally contact each other. This helps forming stable side walls for the three-dimensional basin in dry and wet state. It may be advantageous to have a combination of different type of winglets to provide for a better folding of the side portions, in particular the winglets may have different lengths as measured in the longitudinal direction and/or different shape to provide an improved side seal. The shape and number of winglets may be adapted for different sizes of absorbent articles, and for the different stage of development of the wearer. Each side portion may comprise for example from 3 to 10 winglets, in particular from 4 to 8 winglets.

Absorbent Core's Folding Guides 261, 262

The central portion 60 and the first side portion 61 are separated by a first folding guide 261, and likewise the central portion 60 and the second side portion 62 are separated by a second folding guide 262. The folding guides facilitate the folding of the absorbent core so that the core forms a three-dimensional shape similar to a basin, as illustrated in FIG. 2, when it is placed on the wearer. The side portions of the absorbent material layer form the side walls of the basin while the front and back sides of the central portion are tilted upwards towards each other. The folding guides may in particular be areas substantially free of absorbent material between the central portion and the side portions. The width of absorbent material-free areas may be substantially constant through the folding guides or may vary, for example the width of the material-free areas may gradually increase towards one or both extremities of each of the folding guides. As represented in FIG. 6, the top layer 16 of the core wrap may be advantageously bonded to the bottom layer 16' through the folding guides. This bond 70' may be for example an adhesive bond, a mechanical bond, a fusion bond, an ultrasonic bond or any combinations of these, formed in the areas of the folding guides as indicated previously. The core wrap may also be bonded in other areas of the core, for example in the areas or gaps between the winglets 70", and also to form the C-wrap seals 72 along the longitudinally-extending side edges of the core, as shown on FIG. 6.

The folding guides may advantageously be curved towards the central portion 60. The recesses along the longitudinal sides of the central portion, the proximal edges of the side portions and the folding guides may generally run parallel to each other. In particular, both extremities of each folding guides may completely extend to the longitudinally-extending side edges of the absorbent layer, as illustrated in FIG. 5, thus separating the central portion from the side portions along their whole length, when the article and core are considered in a flattened out configuration. In other words, the folding guides are advantageously not completely surrounded by absorbent material. In this way, the side portions can easily fold relative to the central portion to provide the upstanding side walls of the basin in the folded basin configuration. The folding guides may be curved along a smooth curve without inflexion points, as in a couple of inverted brackets:) (. It is also possible that each of the folding guides may form a curve or a series of segments having an inflexion point at their closest position from each other, for example each being generally "v" shaped with a 90° rotation, thus appearing together as a pair of sign bigger than and smaller than: > <.

The folding guides may be entirely continuous as illustrated in FIGS. 5 and 11, but it is not excluded that the folding guides are intermittently formed, for example by a series of discrete material free areas or embossed areas each separated by small gaps comprising absorbent material, as long as the discrete sections are sufficiently close and aligned to provide for the desired folding guide function.

The folding guides may be more generally provided by any means known in the art, for example as disclosed in WO2006/068549A1 (Hansson) and have any shape, in particular be straight and parallel to the longitudinal direction 80. The folding guides may be for example grooves or channels having a certain width, for example from 1 mm to 20 mm, and comprising either no absorbent material (as illustrated in FIG. 6) or some absorbent material at a lower basis weight than the surrounding areas of the absorbent layer, for example having a basis weight which is from 10% to 80%, in particular 15% to 70%, of the basis weight of the immediately adjacent central portion and/or side portions. A folding guide may be also provided by embossing an absorbent material which is permanently compressible such as a fibrous absorbent material or foam. In this case, the folding guides may be formed by grooves having a higher degree of compression than the surrounding areas of the absorbent layer. It is also known to form folding guides by slitting the material of an absorbent layer, if the absorbent material can be slit such as some solid foam-like absorbent material. Of course a combination of these means can be used to form the folding guides. The folding guides have a centerline generally following the guides along their middle, as shown in dotted line on FIG. 5.

Absorbent Material

The absorbent layer comprises an absorbent material. The absorbent material may be the same in the central portion 60 and the side portions 61, 62, for simplicity of manufacture, but it is not excluded that different materials are used in the central portion and the side portions for example. The absorbent material may typically comprise a high proportion of superabsorbent polymer (herein abbreviated as "SAP"). The term "superabsorbent polymer" refers herein to absorbent materials, which may be cross-linked polymeric materials, and that can absorb at least 15 times their weight of an aqueous 0.9% saline solution as measured using the Centrifuge Retention Capacity (CRC) test (EDANA method WSP 241.2-05E). The SAP may in particular have a CRC value of from 20 to 50 g/g, or from 25 to 40 g/g. The SAP may in particular be in particulate forms (SAP particles) but other forms are also possible, such as absorbent foam or fibers. Further detailed examples of absorbent material, in particular SAP, are disclosed in WO2014/093310 (Ehrnsperger). In particular, the absorbent material may comprise or consist of SAP particles that require a time to reach an uptake of 20 g/g (T20) of less than 240 s as measured according to the K(t) test method described in WO2012/174026 (Ehrnsperger). The SAP particles used may have a permeability at equilibrium expressed as UPM (Urine Permeability Measurement) value of at least $10 \times 10^{-7}$ $(cm^3 \cdot s)/g$, in particular at least $15 \times 10^{-7}$ $(cm^3 \cdot s)/g$, or at least $20 \times 10^{-7}$ $(cm^3 \cdot s)/g$, or from 10 to $50 \times 10^{-7}$ $(cm^3 \cdot s)/g$, as measured by the test method indicated in WO2012/174026A1.

The absorbent core may be in particular substantially free of cellulose fibers, comprising less than 15% by weight of cellulose fibers relative to the total weight of absorbent material, in particular less than 10%, or less than 5% and down to 0% by weight of cellulose fibers. The absorbent core may thus be relatively thin, in particular thinner than conventional cores comprising cellulosic fibers. In particular, the caliper of the core (before use) as measured at the point corresponding to the crotch point C of the article, or advantageously at any points of the surface of the core, may be from 0.25 mm to 5.0 mm, in particular from 0.5 mm to 4.0 mm, as measured according to the Thickness Measurement Method described further below.

The absorbent material layer may be continuous in the central portion and the side portions, as exemplary illustrated in FIG. 5. A continuous layer of absorbent material may in particular be obtained by the addition of two discontinuous absorbent sub-layers as taught in US2008/312617 (Hundorf), the first absorbent sub-layer including a first substrate and the second absorbent sub-layer including a second substrate, the first and second absorbent sub-layers further including superabsorbent particulate polymer material deposited on said first and second substrates and thermoplastic adhesive material covering the absorbent particulate polymer material on the respective first and second substrates. The first and second absorbent sub-layers are combined together such that at least a portion of said thermoplastic adhesive material of said first absorbent sub-layer contacts at least a portion of the thermoplastic adhesive material of the second sub-absorbent layer, the resulting absorbent particulate polymer material layer between the first and second substrates may be thus substantially continuously distributed across the absorbent particulate polymer material area. It is also not excluded that the central and side portions may comprise a multiplicity of land areas comprising the absorbent material, with absorbent material-free junction areas in-between, as is known in the art for example in US2008/312625 (Hundorf).

The basis weight (amount deposited per unit of surface) of the absorbent material may also be varied to create a macroscopically profiled distribution of absorbent material in the longitudinal direction and/or the transversal direction. Typically the absorbent material of the core may be advantageously distributed in somewhat lower amount towards the back edge of the core as more absorbency is typically required towards the front and middle region of the core. Further detailed examples of absorbent material distribution that can be used herein are disclosed in WO2014/093310 (Ehrnsperger). The side portions may comprise an absorbent material at a constant basis weight or may also have a profiled distribution. The central portion may typically comprise a larger overall amount of absorbent material than the two side portions combined, for example in a ratio ranging from 20:1 to 2:1.

The absorbent material may be deposited on a substrate to form the central portion and the side portions by adapting any known processes that allow relatively precise deposition of absorbent material, in particular SAP, advantageously at relatively high speed. The absorbent material may be deposited for example using a SAP printing technology as disclosed in US2006/024433 (Blessing), US2008/0312617 and US2010/0051166A1 (both to Hundorf et al.). This technique uses a transfer device such as a printing roll to deposit SAP particles onto a substrate disposed on the grid of a support (e.g. a lay-on drum). The grid may include a plurality of cross bars extending substantially parallel to and spaced from one another so as to form ribs extending between the cross-bars. The SAP is deposited in the undulations of the substrate inside these ribs. As known in the art indicated above, two such SAP printing roll/laying-on drum systems working in parallel can be used to print twice a SAP layer on two substrates, the substrates being then assembled with the SAP layers in contact with each other thus forming a continuous layer of SAP between a top layer and a bottom layer (the core wrap). This technology allows high-speed and precise deposition of SAP on a substrate in a desired pattern.

US2012/0312491 (Jackels) more recently discloses how raised elements on the transfer device may collaborate with corresponding mating strips on the support grid to provide areas free of deposited absorbent material. Such raised elements can serve to form the folding guides of the invention. Additional raised elements can further help forming the gaps between the winglets. The top and bottom layers of the core wrap can be bonded together through some of these material-free areas to form the folding guides and the gaps between the winglets. Thus a SAP printing technique may be advantageously used to make absorbent cores according to the invention. Of course it is not excluded that other manufacturing techniques may be used, or that products are hand-made for research purpose for example.

Further Components of the Absorbent Core

The absorbent core may optionally comprise one or more layers of glue to help immobilizing the absorbent material and/or form bonds between the layers of the core wrap, for example as disclosed in US2006/024433 (Blessing), US2008/0312617 and US2010/051166A1 (both to Hundorf et al.) and US2012/0312491 (Jackels). The absorbent core may in particular comprise at least one auxiliary glue layer 70 applied on the inner side of the top layer 16 and/or the bottom layer 16' of the core wrap. The auxiliary glue may be applied directly over the substrate on which the absorbent material is subsequently deposited, thus at least partially immobilizing the absorbent material on the substrate. The auxiliary glue may also have for function to at least partially form the core wrap bond 70' within the folding guides, in particular through the material free areas 261, 262, and/or bonds 70" in the gaps between the winglets and transversally outward of the side portion. The auxiliary glue 70 may also help forming C-wrap bond 72 between the core wrap layers, whereas a different, stronger glue may be used for these bonds 72. The auxiliary glue may also be useful to improve the adhesion of a fibrous thermoplastic adhesive material, when present, to the substrate.

Figure 7:
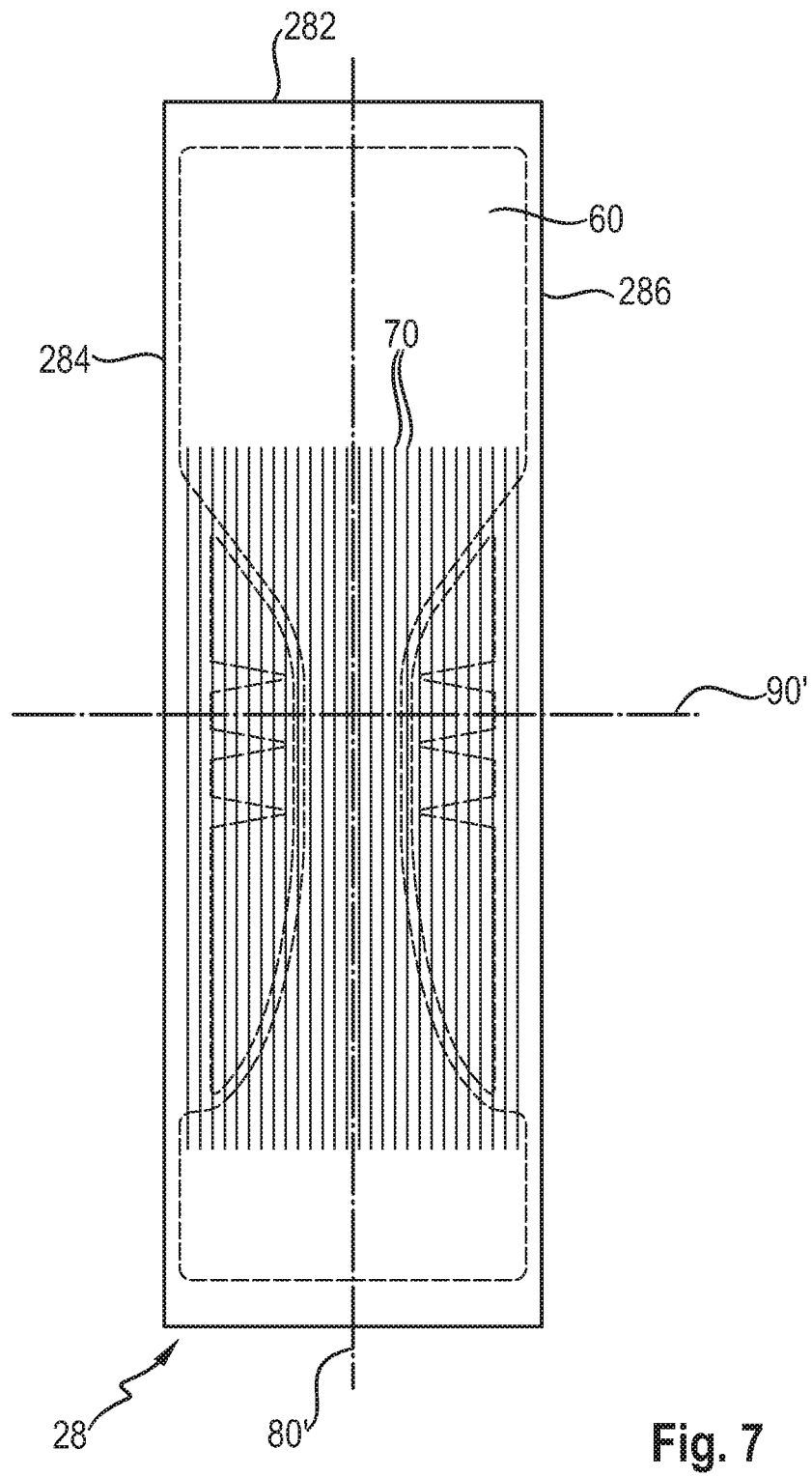
FIG. 7 shows an exemplary glue application pattern on the inner side of the top layer of the absorbent core with the absorbent layer in dotted lines.

FIG. 7 shows an exemplary application pattern of a glue layer, referred to herein as auxiliary glue 70, which may be used to provide for bonds 70' between the top layer 16 and the bottom layer 16' in the folding guides and for bonds 70" in the areas of the gaps between the winglets 70"'. The glue used may be any hotmelt adhesive known in the art. The glue layer may be applied on the inner surface of the top layer 16 and/or the bottom layer 16' of the core wrap. The auxiliary glue may be applied directly over the substrate layer on which the absorbent material is subsequently deposited, thus at least partially immobilizing the absorbent material on the substrate. The auxiliary glue is applied over an application area of the layer. The glue application area may for example cover at least the whole of the folding guides and the side portions to provide for a bonding in these areas of the top layer and the bottom layer. As represented in FIG. 7, the glue application area can also be shorter than the central portion to reduce the usage of adhesive material, however it is not excluded that the glue application area may be as long as or longer than the central portion.

The auxiliary glue can be applied by any adhesive applicator known in the field, in particular bead, slot or spray nozzles. For example, as represented, the auxiliary glue can be applied using a slot coating process as a pattern comprising a plurality of spaced-apart glue slots which may each extend in the longitudinal direction. The slots may for example have a width of from 0.5 mm to 3 mm, and/or have a lateral spacing there-between of from 0.5 mm to 4 mm.

The absorbent core may also comprise a fibrous thermoplastic adhesive material (not shown), also known as microfibrous glue, to help immobilizing the absorbent material within the core wrap. The fibrous thermoplastic adhesive material may be applied, typically by spraying, over an absorbent material layer that has been discontinuously deposited on a substrate during the core making process, thus forming land and junction areas as indicated above. The fibrous thermoplastic adhesive material contacts the absorbent material and the substrate layer in the absorbent material free junction areas. This imparts an essentially three-dimensional net-like structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material, and thereby immobilizes this absorbent material. A dual layer core can thus be constructed wherein the land areas of one layer correspond to the material-free junction areas of the other layer and vice versa, resulting in continuous dual absorbent layer.

The adhesive material may advantageously help providing a high immobilization of the absorbent material in dry and wet state. The absorbent core advantageously achieve an SAP loss of no more than about 70%, 60%, 50%, 40%, 30%, 20%, or 10% according to the Wet Immobilization Test described in US2010/051166A1.

Liquid Management Layer(s) 52, 54

The article may advantageously comprise at least one liquid management layer at least partially present between the topsheet and the absorbent core. Liquid management layers function to quickly acquire and/or distribute the fluid away from the topsheet and into the core. These liquid management layers are sometimes called "wicking layer", "surge layer", "acquisition layer" or "distribution layer". Typically, liquid management layers do not comprise SAP, as this may slow the acquisition and distribution of the fluid. The prior art discloses many type of liquid management layer, see for example WO2000/59430 (Daley), WO95/10996 (Richards), U.S. Pat. No. 5,700,254 (McDowall), WO02/067809 (Graef). Liquid management layers are typically placed symmetrically relative to the longitudinal axis of the article, but other configurations are possible. The liquid management layers may be typically shorter at least in the longitudinal dimension and typically also in the transversal direction relative to the absorbent material layer of the absorbent core.

Liquid management layers help improving the fluid handling properties of the article, in particular for those articles having no or relatively little cellulose fibers in the absorbent core. Cellulose fibers can typically help acquiring and distributing the fluid within the core. In the present invention, where the absorbent material of the core may be substantially free of cellulose fibers, it is thus advantageous to have at least one liquid management layer. The inventors have however found that conventionally shaped liquid management layer may hinder the absorbent core from forming the desired basin shape.

Figure 8:
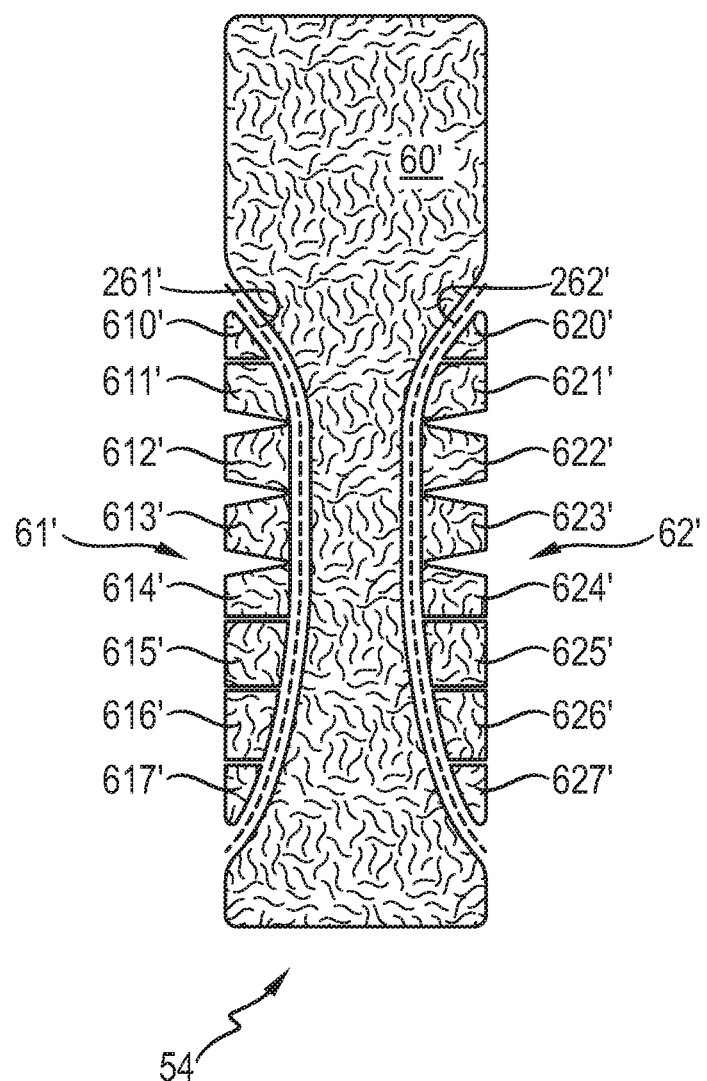
Figure 9:
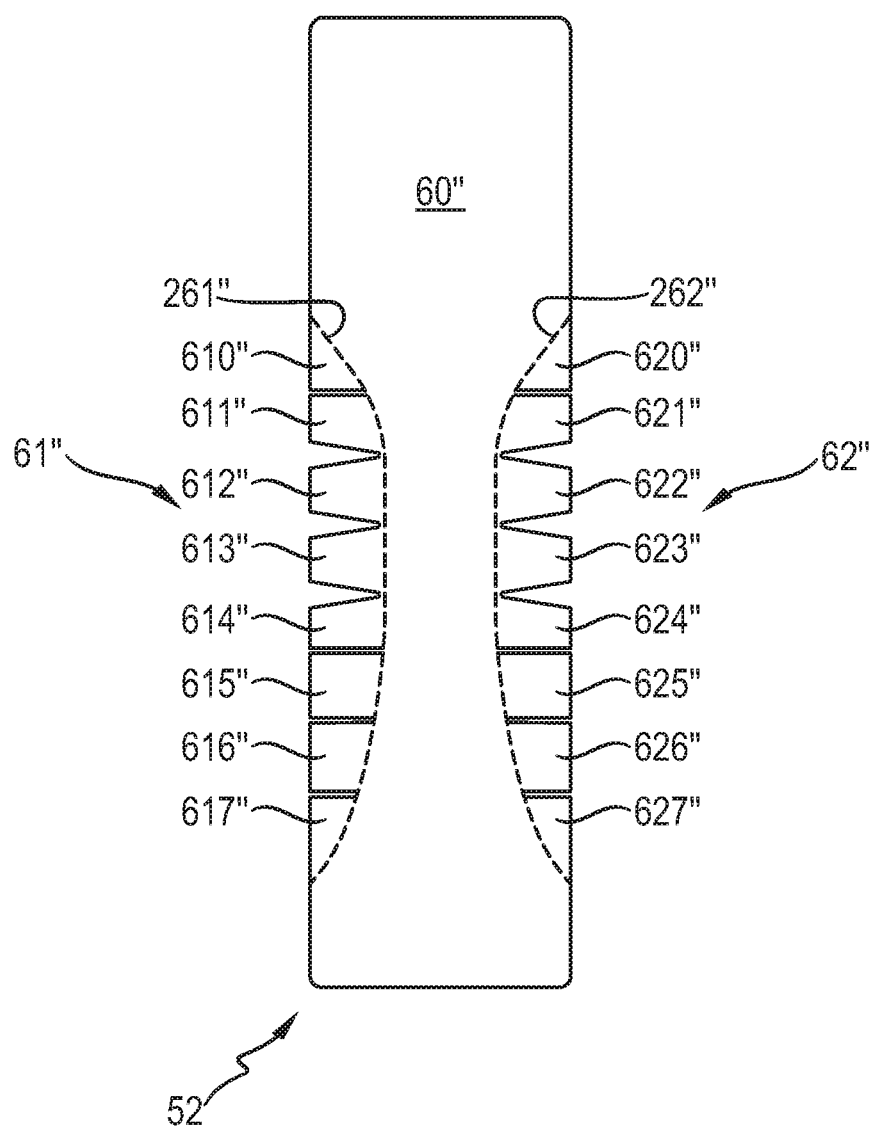
Figure 10:
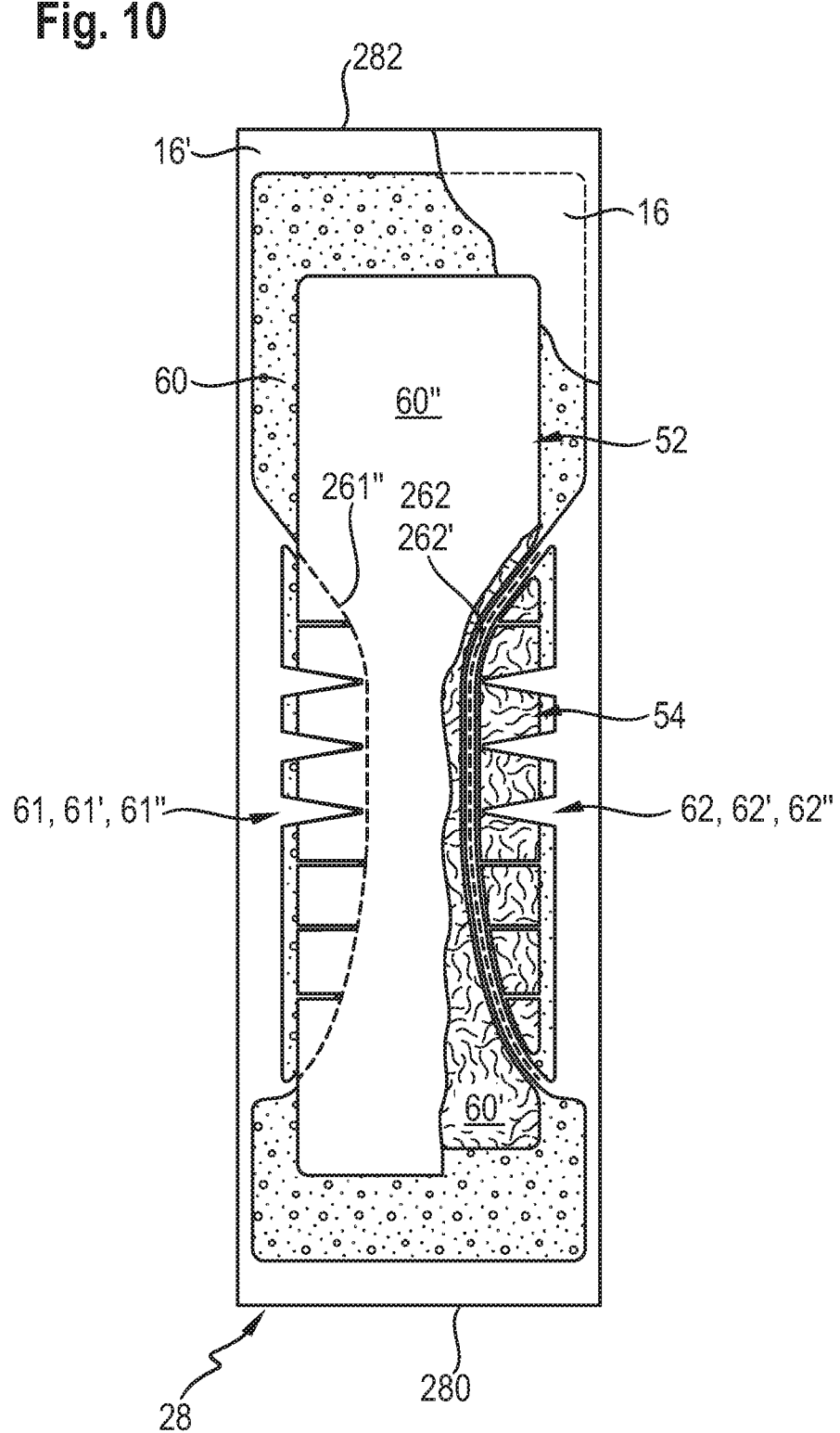
FIG. 10 is a top view of the absorbent core, and two liquid management layers of FIG. 1 shown in superposition.

When present, the liquid management layer(s) may thus comprise folding guides which are at least partially superposed with the folding guides of the absorbent core. Thus the liquid management layer can easily fold in a similar manner than the core when it forms the three-dimensional basin. As illustrated in FIGS. 8-9, the liquid management layers may optionally also comprise a central portion 60', 60", a first and second side portions 61'-62', 61" 62", and a first and second folding guides 261'-262', 261"-262". The liquid management layer's folding guides, when present, may be at least partially superposed with the folding guides of the absorbent core. By "generally superposed", it is meant that the position and shape of the folding guides of the liquid management layer vertically correspond to the underlying folding guides of the absorbent core, so that the liquid management layer can readily assume the shape of the basin formed by the underlying absorbent core when the article is put on and worn by the wearer. It is not necessary that the folding guides of the two layers are exactly superposed, and there may be for example a slight transversal shift due to the unavoidable process tolerance in modern high speed making process or to take into account the thickness of the layers when forming the three-dimensional basin. Thus it may be acceptable that the center lines of both folding guides are within a distance of 10 mm or less, for example 5 mm, from each other when considered in the plane of the article. As illustrated in the drawings, the liquid management layer's folding guides may be superposed with the folding guides of the absorbent core over the whole length of the liquid management layer's folding guides, but a lower percentage of overlap is also possible. It is not excluded that there may be areas where the folding guides of these layers do not overlap, or the folding guides of one layer may be shorter than the folding guides of another layer. For example, the liquid management layer's folding guides may overlap over at least 50%, 60%, 70% or more of the overall length of the absorbent core's folding guides. In the remaining areas where there is no overlap, the liquid management layer's folding guides may for example be off-set relative to the absorbent core's folding guides, or may be shorter and thus not extend to the same length as the absorbent's core folding guides.

If winglets are present in the side portions of the liquid management layer, these may be constructed in a similar or same configuration as the underlying absorbent core, including the shape of the winglets and the gaps between the winglets. However, it is also considered that when more simple constructions are desired, the liquid management layer's side portions may also comprise no or different winglets. The liquid management layer's side portions may thus also each be comprised of a single piece of liquid management material delimited by a distal straight line and proximal curve, or two curves, which may in particular form crescent-shaped side portions.

Figure 4A:
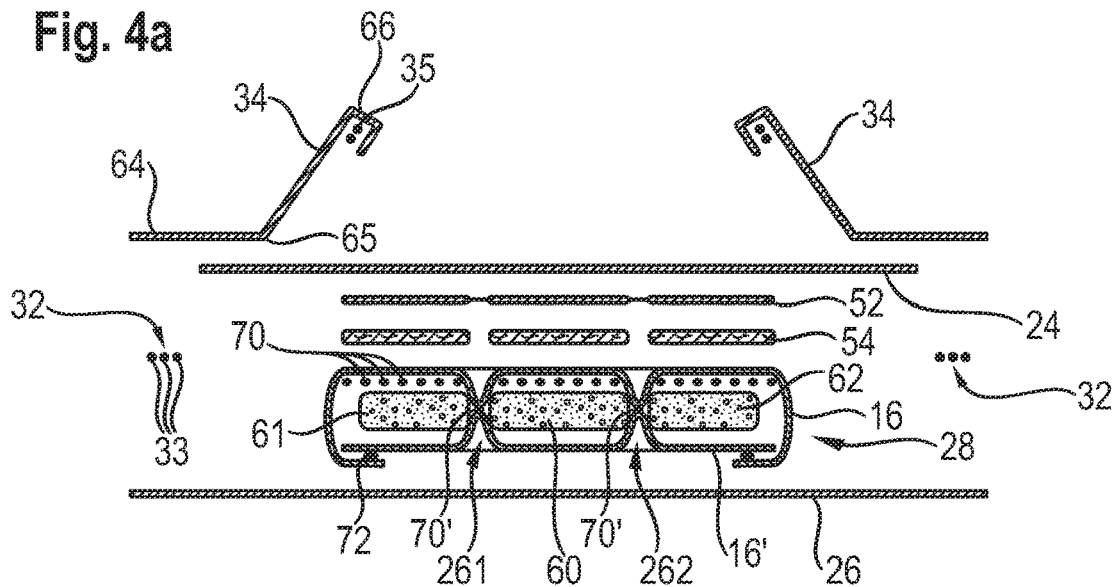
FIG. 4a is a schematic cross-section of the article of FIG. 1 along 4-4.
Figure 4B:
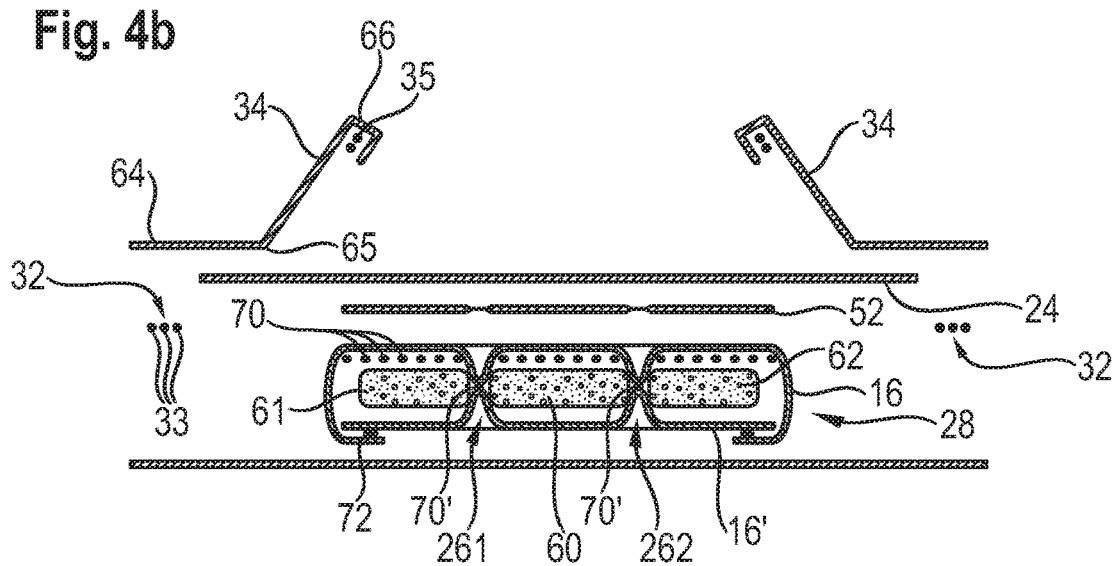
FIG. 4b is a cross-section as in FIG. 4a of a simplified article with only one of the two liquid management layers.
Figure 4C:
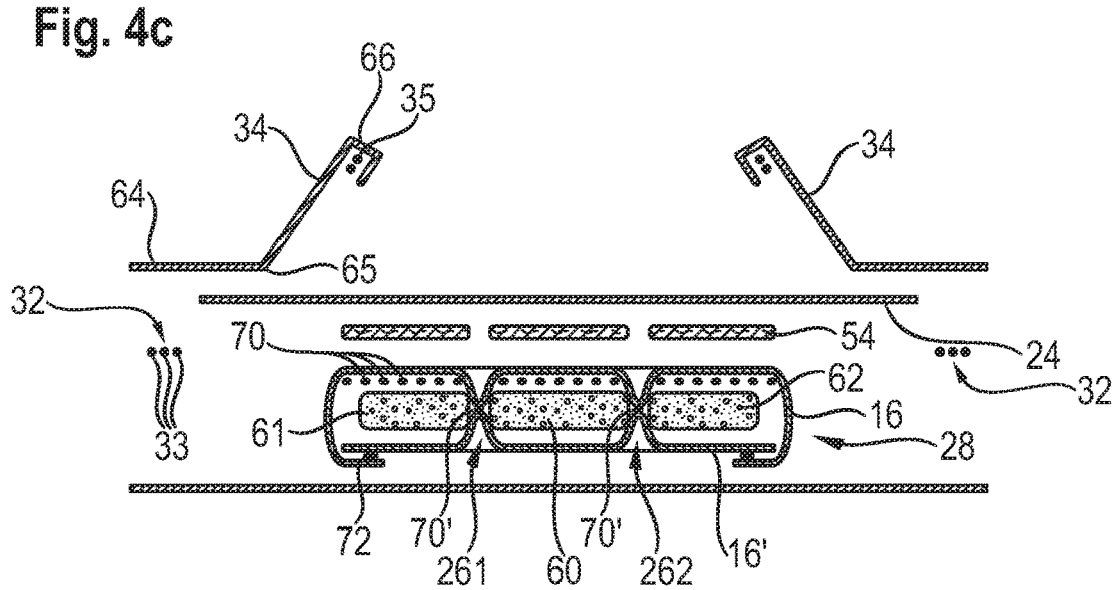
FIG. 4c is a cross-section as in FIG. 4a of another simplified article with the other one of the two liquid management layers present.

The article of the invention may also comprise two or more liquid management layers, and these may form a unitary layer or remain discrete layers, which may be loosely attached to each other. The article may in particular comprise two liquid management layers: an acquisition layer 52 directly under the topsheet and a distribution layer 54 between the acquisition layer and the absorbent core, as illustrated in FIG. 4*a*. Such dual layer liquid management layers are for example disclosed in further details in WO2014/093323 (Bianchi) with a distribution layer comprising cross-linked cellulosic fibers and the acquisition layer a carded, resin-bonded nonwoven. The invention is however not restricted to this example having two liquid management layers. The majority of articles have in particular for cost reason only one liquid management layer. FIG. 4*b* for example shows such an absorbent article comprising only an acquisition layer 52. FIG. 4*c* shows another example of absorbent article comprising only a distribution layer 54. As indicated previously, there may also be no liquid management layer between the absorbent core and the topsheet, and/or one such layer may be present under the absorbent core, between the absorbent core and the backsheet.

The article may also comprise a liquid management layer that does not have folding guides. Some liquid management layers are made of material relatively flexible and bendable so that they do not prevent to a substantial extent the underlying absorbent core from folding in the basin shape. A further liquid management layer having a width inferior or equal to the width W3 of the central portion of the absorbent core between the side portions may also be provided without expected negative effect on the folding of the absorbent core.

The following will describe in more details two examples of liquid management layers according to the invention, which may be respectively used as an acquisition layer 52 and a distribution layer 54 alone in an article (as illustrated in FIG. 4*b* and FIG. 4*c*) or in combination (as illustrated in FIG. 4*a*).

FIG. 8 shows an exemplary liquid management layer 54 in isolation. This layer may for example primarily function as a distribution layer, although this is not to be considered limiting. The function of a distribution layer is to spread the insulting fluid liquid over a larger surface within the article so that the absorbent capacity of the core can be more efficiently used. Typically, distribution layers can be made of a material comprising synthetic or cellulosic fibers and having a relatively low density. The distribution layer material may be a nonwoven or a fibrous layer comprising unbound or loosely bound hydrophilic fibers, in particular a layer of cross-linked cellulosic fibers. The density of the distribution layer may vary depending on the compression of the article, but may typically range from 0.03 to 0.25 g/cm$^3$, in particular from 0.05 to 0.15 g/cm$^3$ measured at 0.30 psi (2.07 kPa). The distribution layer may also be a material having a water retention value of from 25 to 60, preferably from 30 to 45, measured as indicated in the procedure disclosed in U.S. Pat. No. 5,137,537.

In a particular example, the liquid management layer 54 may comprise at least 50% by weight, optionally consisting of 100%, of cross-linked cellulosic fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf), however not in the manner of the invention. The cross-linked cellulosic fibers provide higher resilience and therefore higher resistance against the compression in the product packaging or in use conditions, e.g. under baby weight. This provides the layer with a higher void volume, permeability and liquid absorption, and hence reduced leakage and improved dryness. The liquid management layer 54 may also be typically profiled so that more material is present at the front and middle part of the article relative to the back of the article. The distribution layer may typically have an average basis weight of from 30 to 400 g/m$^2$, in particular from 100 to 300 g/m$^2$, with the basis weight varying along the length of the article so that more material is present at the front and middle of the layer than at the back. The liquid management layer 54 may thus be profiled and/or shaped rounded towards the back of the article, as exemplarily disclosed in WO2014/093323 (Bianchi).

As indicated above, the liquid management layer may generally follow the contour and construction of the absorbent core over which it is disposed, although it may also be in general shorter in longitudinal and/or transversal direction. In general, the same features disclosed previously for the central portion, side portions and folding guides of the core can apply to the liquid management layer. The liquid management layer may thus comprise as represented in FIG. 8, a central portion 60' extending longitudinally, but which may be shorter than the central portion 60 of the core, and two folding guides 261', 262'. These folding guides may be made as indicated previously for the folding guides 261, 262 of the core, in particular and as illustrated in FIG. 8, they may comprise areas substantially free of the liquid management material, in this case substantially free of unbound or loosely bound hydrophilic fibers such as cross-linked cellulosic fibers.

The liquid management layer's side portions 61', 62' may further comprise winglets 610'-617', 620'-627', which as shown may generally correspond in shape and configuration to the winglets 610-613, 620-623 of the absorbent core. As illustrated in FIG. 8 and FIG. 9, the liquid management layer may in addition to the triangular gaps between the winglets also comprise straight gap having a constant width along their length, which may be described as slits (as illustrated by the gaps between the winglet pairs 610'-611', 614'-615', 615'-616', 616'-617'). These slits may provide additional flexibility of the liquid management layer while the small distance between the winglets ensures optimal fluid acquisition and distribution.

In general, the liquid management layer's folding guides, central portion and side portions may form a three-dimensional basin similar to the one formed by the core when put on the wearer. When winglets are present in the liquid management layer, these may also form better fitting side walls for three-dimensional basin. However it is believed that the loosely bound fibers forming such a layer 54 may be sufficiently conformable so that winglets in the liquid management layer are not necessary. Each liquid management layer's side portions may thus alternatively have a more simple shape, such as crescent-shaped or semi-circular, with the proximal the edge parallel to the liquid management layer folding guide and the distal edge straight and parallel to the longitudinal direction.

Such a fibrous distribution layer 54 may for example be made on-line by depositing the fibers, for example cross-lined cellulosic fibers, on a forming surface having ridges corresponding to the areas where no fibrous material is desired. Deposition chambers are known wherein a carrier sheet is provided on a forming surface having a series of holes connected to a vacuum, so that the vacuum pulls the fibers in the desired emplacements to form a desired deposited layer. The forming surface of these deposition chambers can be modified to provide a layer of fibrous material according to the invention having a central portion, side portions separated by folding guides and optionally winglets. The fibrous layer is typically formed or transferred on a carrier sheet, which should thus have at least the same dimension as a fibrous liquid management layer. The carrier sheet may be the topsheet, another liquid management layer such as a nonwoven acquisition layer 52, or any other layer of the article, for example the core wrap.

FIG. 9 illustrates another example of liquid management layer 52 that can be used in the present invention. This liquid management layer 52 may for example be used as an acquisition layer in the article, and may be used alone or in combination with another liquid management layer such as a liquid management layer/distribution layer 54. The liquid management layer 52 illustrated in FIG. 9 may be made of a nonwoven web rather than loosely bound fibers as for the layer 54 discussed before. The nonwoven web may be for example provided as a continuous roll of material that is cut according to the desired length and pattern as it unwound in a converting line.

A "nonwoven web" or "nonwoven" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m² or gsm).

The acquisition layer 52 is typically placed directly under the topsheet, and above a distribution layer if such a layer is present. The acquisition layer may typically be or comprise a nonwoven, for example a through-air bonded ("TAB") carded nonwoven, a resin-bonded ("RB") carded nonwoven, a spunbond or spunlace (hydroentangled) nonwoven. TAB carded nonwovens may for example be made from soft PE/PP bicomponent staple fibers. The air through bonding process locks in loft and resistance to compression. Resin-bonded carded nonwovens may be made from multi-denier polyester staple fibers (for example: 50/50 or 40/60 mix of 6 denier and 9 denier fibers). Their resilient and open structures are designed to provide excellent fluid acquisition properties. Such acquisition layers are available directly from suppliers, e.g. Fitesa of Simpsonville, S.C., USA or TWE Group GmbH, of Emsdetten, Germany. The resin used to stabilize the nonwoven layer may typically be a latex binder, for example a styrene-butadiene latex binder (SB latex). Processes for obtaining such latexes are known, for example from EP149,880 (Kwok), US2002/028858 and US2003/0105190 (Diehl). The binder may typically be present in an acquisition layer in excess of about 12%, about 14% or about 16% by weight of the layer. A SB latex is for example commercially available under the trade name GEN-FLO™ 3160 (OMNOVA Solutions Inc.; Akron, Ohio). Latex bonded acquisition layers are for example further disclosed in US2005/033252A1, US2005/033253A1 or US2005/043694A1 (Schneider). The basis weight of acquisition layers may typically range from 10 gsm to 200 gsm, in particular 20 gsm to 140 gsm, or 40 gsm to 120 gsm, for example 80 gsm.

The liquid management layer 52 as illustrated on FIG. 9 comprises a central portion 60" and side portions 61", 62". The side portions 61", 62" may in turn also comprise winglets 610"-617", 620"-627", although it is not excluded that the side portions do not comprise winglets but are each crescent-shaped or otherwise shaped as indicated previously for the liquid management layer 54. For a liquid management layer formed from a nonwoven material, as illustrated on FIG. 9, it may be more practical to form the liquid management layer folding guides 261", 262" by compressing or slitting the nonwoven material according to desired pattern. This is exemplarily represented on FIG. 9 by the folding guides 261", 262" which follow the contour of the folding guides of the absorbent core 28 and are exemplarity formed by intermittently slitting the layer 52. The winglets may be formed by cutting triangular cut-outs or slitting the side portions in the transversal direction to form gaps between the winglets 610"-617", 620"-627". These cuttings or slitting operations may be made online using conventional tools such as slitting tools, embossing tools or cutting tools.

A further acquisition layer (not represented) may be used in addition to a first acquisition layer described above. For example a tissue layer may be placed between the acquisition layer 52 and the distribution layer 54. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

Topsheet 24

The topsheet may be any topsheet known in the art for absorbent articles. The topsheet is preferably compliant, soft-feeling, and non-irritating to the wearer's skin. Further, at least a portion of the topsheet is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8. Typical diaper topsheets have a basis weight of from about 10 to about 28 gsm, in particular between from about 12 to about 18 gsm but other basis weights are possible.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T".

The topsheet may also be treated with a wetting agent to make it more hydrophilic. The wetting agent may be a surfactant as is known in the art. Other possible treatments are for example special coating by nanoparticles, as for example described in U.S. Pat. Nos. 6,645,569, 6,863,933, US2003/148684 and US2005/008839, (Cramer et al.) and U.S. Pat. No. 7,112,621 (Rohrbaugh et al). Any portion of the topsheet may also coated with a lotion as is known in the art. Examples of suitable lotions include those described in U.S. Pat. Nos. 5,607,760, 5,609,587, 5,643,588, 5,968,025 and 6,716,441. The topsheet 24 may also include or be treated with antibacterial agents, some examples of which are disclosed in WO 95/24173. Further, the topsheet, the backsheet or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 cm$^2$ and about 50 cm$^2$, in particular between about 15 cm$^2$ and 35 cm$^2$. Examples of apertured topsheet are disclosed in U.S. Pat. No. 6,632,504. WO 2011/163582 also discloses suitable colored topsheet having a basis weight of from 12 to 18 gsm and comprising a plurality of bonded points. Each of the bonded points has a surface area of from 2 mm$^2$ to 5 mm$^2$ and the cumulated surface area of the plurality of bonded points is from 10 to 25% of the total surface area of the topsheet.

Although not shown in the drawings, it is possible to bond the topsheet directly or indirectly to the folding guides of the absorbent core. If a liquid management layer is present between the topsheet and the backsheet, the topsheet may also be bonded to or through the folding guide of the liquid management layer. The topsheet may be bonded by any known bonding means, typically adhesive bonding, pressure bonding or heat bonding, or a combination of these. Similarly the topsheet may also be directly or indirectly bonded to at least some of the areas of the core wrap corresponding to the gaps between the winglets of the absorbent core.

Backsheet 25

The backsheet 25 may also be made according to any backsheet known in the art for absorbent articles. The backsheet is typically impermeable to liquids (e.g. urine) so that it keeps the garment-facing side of the article dry. The backsheet may for example be or comprise a thin plastic film such as a thermoplastic film having a thickness of less than about 0.10 mm. Exemplary backsheet films include those manufactured by Tredegar Corporation, based in Richmond, Va., and sold under the trade name CPC2 film. Other suitable backsheet materials may include breathable materials which permit vapors to escape from the article while still preventing exudates from passing through the backsheet. A covering low basis weight nonwoven may be attached to the external surface of the film to provide for a softer touch.

Other Components of the Article

The absorbent articles of the invention can comprise any typical components known for the intended purpose of the article. FIG. 1 and FIG. 3 show other typical taped diaper components not further discussed herein such as a fastening system comprising fastening tabs 42 attached towards the back edge 12 of the article and cooperating with a landing zone 44 placed towards the front edge 10 of the article. These fastening features are typically absent from pant-type articles which have a pre-formed side seam, nevertheless the invention may of course also be used in such pant-types articles. The absorbent article may also comprise other typical components, which are not represented in the Figures, such as a back elastic waist feature, a front elastic waist feature, transverse barrier element across the topsheet, a wetness indicator between the core and the backsheet that changes appearance when contacted with urine, a lotion application on the topsheet, etc. These components are well-known in the art and will not be further discussed herein. Reference is made to WO2014/093310 where several examples of these components are disclosed in more details.

The absorbent articles may typically further comprise components that improve the fit of the article around the legs of the wearer, in particular a pair of barrier leg cuffs 34 and gasketing cuffs 32. The barrier leg cuffs 34 may each be formed by a piece of material, typically a nonwoven, that can be partially raised away and thus stand up from the plane defined by the topsheet, as shown for example in FIGS. 4a-c. The barrier leg cuffs thus comprise a first portion 64 flush with the topsheet and limited inwardly by a proximal edge 65. This first portion may be attached to the topsheet and/or backsheet with an intermittent or continuous fusion bond and/or a glue bond. The barrier leg cuffs 34 further comprise a free-standing portion limited by a distal edge 66, which in use fits at the junction of the thighs with the torso of the wearer, at least in the crotch region 37 of the article. The barrier leg cuffs can provide improved containment of liquids and other body exudates approximately at the junction of the torso and legs of the wearer. Typically, the barrier leg cuffs are formed from a separate material joined to the rest of the article, in particular to the topsheet, but it is not excluded that the barrier leg cuffs can be integral with (i.e. formed from) the topsheet or the backsheet, or any other layer, for example the bottom layer of the core wrap. Typically the material of the barrier leg cuffs may extend through the whole length of the article but is further bonded to the topsheet towards the front edge and back edge of the article so that in these sections the barrier leg cuff material remains flush with the topsheet (tack bonds not shown in FIG. 1 for readability). Each barrier leg cuff 34 typically comprises one, two or more elastic strings 35 close to this free standing terminal edge 66.

The contractive elastic forces provided at the distal end 66 of the barrier leg cuffs can help folding the absorbent core and thus the absorbent article into a basin shape. Thus the elastic strings 35 will not only cause the barrier leg cuffs to stand up, but they will advantageously also pull the side portions 61, 62 of the absorbent core upwards, with these side portions hinging on the folding guides 261,262. When present, the corresponding side portions of a liquid management layer 52, 54 will also stand up to form absorbent side walls.

In addition to the barrier leg cuffs 34, the article may typically comprise gasketing cuffs 32, which may be present as part of the chassis of the absorbent article. The gasketing cuffs may be at least partially enclosed between the topsheet and the backsheet, or the barrier leg cuffs and the backsheet. The gasketing cuffs may be placed transversally outward relative to the proximal edge 65 of the barrier leg cuffs 34. The gasketing cuffs can provide a better seal around the thighs of the wearer. Usually each gasketing cuff will comprise one or more elastic element(s) 33 such as elastic strings embedded within the chassis of the diaper, for example between the topsheet and backsheet in the area of the leg openings. These elastic elements 33 may, independently or in combination with the elastics 35 of the barrier leg cuffs, help shaping the absorbent article into a basin shape when put in place on and being worn by the user.

Various cuff constructions have been disclosed for in the art and may be used in the present invention. U.S. Pat. No. 3,860,003 describes a disposable diaper which provides a contractible leg opening having a side flap and one or more elastic members to provide gasketing cuffs. U.S. Pat. Nos. 4,808,178 and 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. More recently, WO2005/105010 (Ashton) discloses a dual cuff system made of a continuous cuff material. All or a portion of the barrier leg and/or gasketing cuffs may be treated with a lotion.

Although not represented, the article of the invention may further comprise other longitudinally-extending elasticized elements as known in the prior art, in particular elements which may be at least partially placed between the side portions 61, 62 of the absorbent layer and the backsheet, and whose function is to further help folding the article along the folding lines when it is put in place and worn by the user. For example WO2006/068549 (Hansson) discloses having at least two stretchable crotch elastic members in the crotch portion and attached to the absorbent core and/or one of the topsheet or backsheet, wherein at least a substantial portion of the crotch elastic members are positioned laterally outside the respective folding guides. WO95/16418 (Wildlund) discloses having two elastic threads fastened in a stretched state to the topsheet and extending from the front of the article to the back of the article. The threads are mutually convergent.

The combined elastic forces provided by the different elasticized components of the article may thus bring or facilitate bringing the article into a basin shape when the article is placed on a wearer.

More generally, adjacent layers within the article will be joined together using conventional bonding method such as adhesive coating via slot coating, spiral gluing, or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers. For example, the backsheet and the core wrap may be glued using a core-to-backsheet gluing pattern as disclosed in WO2012/170341A1 (Hippe), or a full coverage pattern using several spiral glue applicators. If for example the backsheet is attached by gluing or otherwise to the areas of the core wrap corresponding to the folding guides (not shown), the folding guides may become more visible to the user from the garment-facing side of the article. Any typical hotmelt adhesives may be used. It is also possible to use a printed adhesive layer, for example between the topsheet and absorbent core or liquid management layer, which may be optionally visible through the topsheet, as exemplary disclosed in WO2014/078247.

FURTHER EXAMPLE

Figure 12:
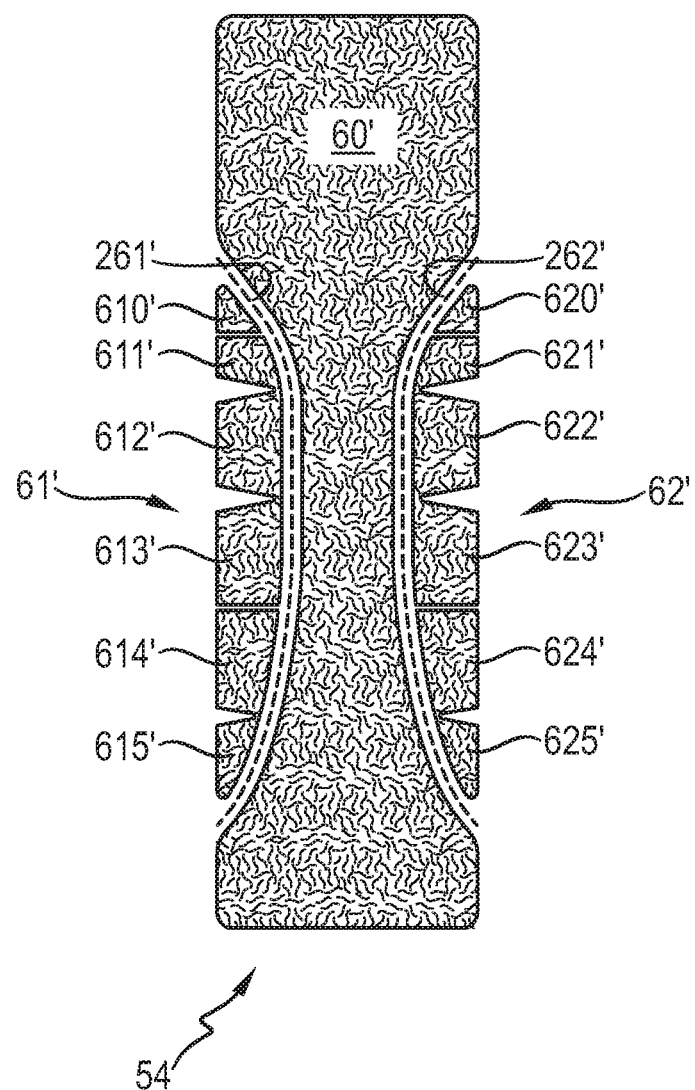
FIG. 12 is a top view of an alternative lower liquid management layer.
Figure 13:
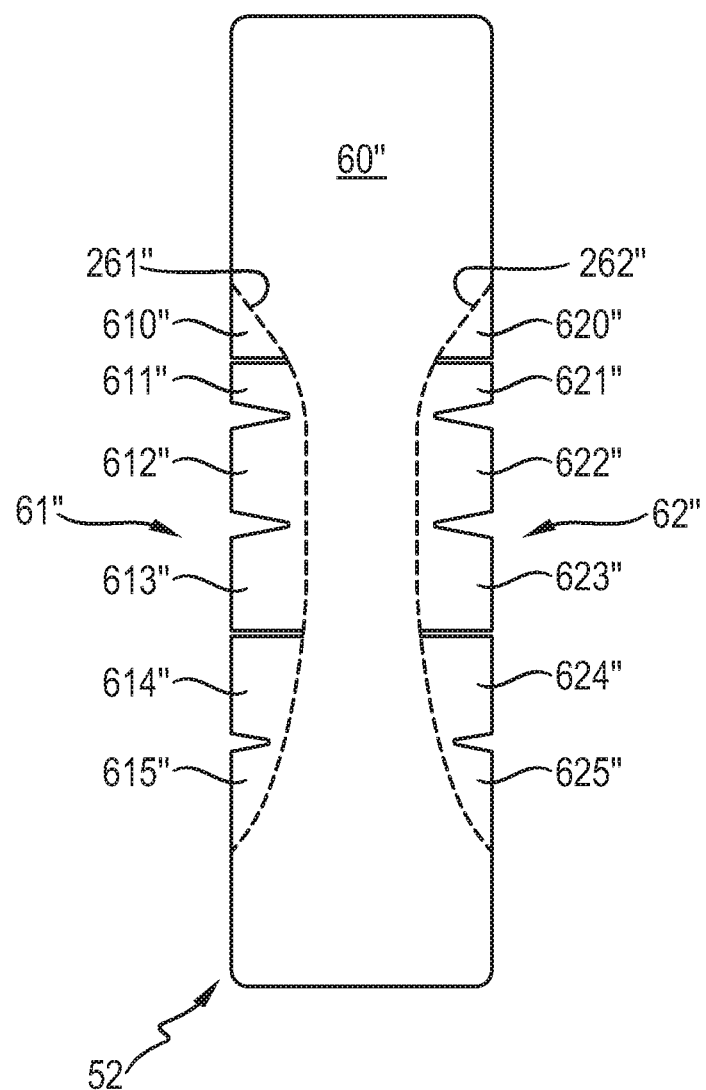
FIG. 13 is a top view of an alternative upper liquid management layer.
Figure 14:
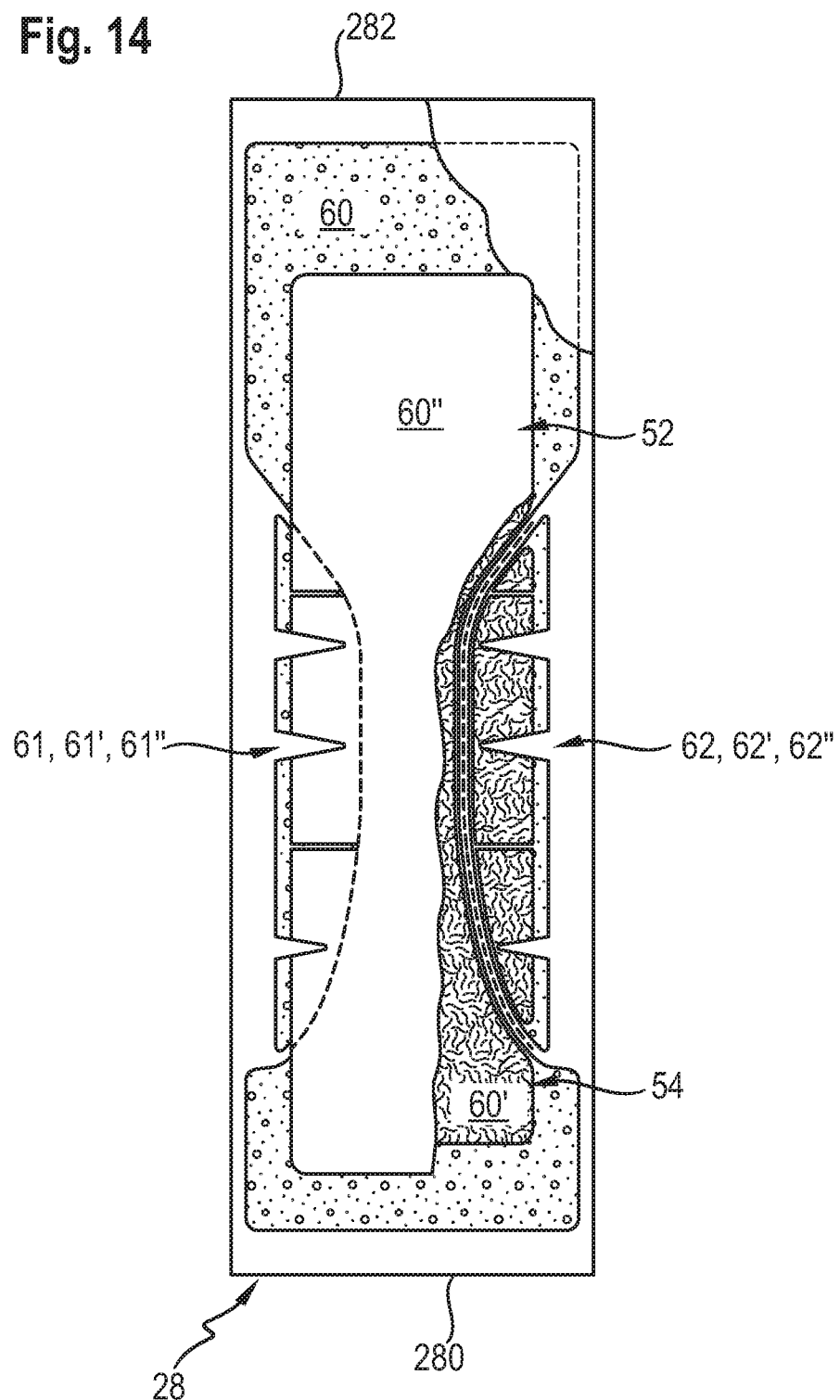
FIG. 14 is a top view of layers of FIGS. 11, 12, 13 shown in superposition.

FIG. 11 illustrates an absorbent core similar to the one shown in FIG. 5 but with a different pattern of gaps separating the winglets. The gaps between the winglets still comprise triangular gaps between neighboring winglets, but in a different arrangement. By changing these arrangements, the shape of the basin may be modified so as to be more suitable for the particular need of the wearer. For example, smaller babies may be spending more time laying on the back or sitting, while more developed babies or toddlers may spend more time standing and walking. This may require a different radius of curvature for the core in the basin configuration. The absorbent core of FIG. 11 and an article in which this core is integrated may follow the same consideration as indicated previously for the core of FIG. 5, in particular an auxiliary glue application pattern on the inner side of the core wrap's top layer 16 of the absorbent core as previously indicated in relation to FIG. 7. FIG. 12 and FIG. 13 illustrate adapted liquid management layers having winglets generally matching the winglets of the core of FIG. 11, with FIG. 14 showing all three layers superposed. However it is clear that these embodiments are not limiting the present invention, in particular it is not excluded that simpler liquid management layers construction having no winglets may be used with the absorbent core of the invention.

Packaging

The absorbent articles may be packaged in any type of conventional packaging. The absorbent articles may be in particular compressed when packaged to save space. The package may thus comprise a plurality of bi-folded absorbent articles, wherein the articles in the package have an in-bag stack height (herein "IBSH") of less than about 80 mm, according to the In-Bag Stack Height Test as described in WO2011/041352 (Weisman et al.), incorporated herein by reference. The packaged absorbent articles may for example have an IBSH of from about 72 mm to about 80 mm or from about 74 mm to about 78 mm, specifically reciting all 0.5 mm increments within the specified ranges and all ranges formed therein or thereby, according to the In-Back Stack Height Test.

Many absorbent articles are bi-folded along their transversal centerline 90 when packed in their bags. When the articles are highly compressed in the bag to save space, this may cause a permanent fold line to appear along the bi-fold line of the articles, depending of the material used and the storage time of the articles in bag. Thus it is also considered that the articles may be packaged under a lower compression to avoid this issue, for example corresponding to an IBSH above 80 mm, in particular between 84 mm and 120 mm. The articles may also be packaged tri-folded, as exemplarily disclosed in WO2008/155702 (Hundorf).

The articles may thus also be packaged at a more moderate compression rate than suggested in some of the prior art, in particular at a In-Bag Compression Rate of from 5% to 45%, in particular from 10% to 40%. The "In-Bag Compression Rate" as used herein is one minus the height of a stack of 10 folded articles in millimeters, measured while under compression within a ply-bag ("In-Bag Stack Height"), divided by the height of a stack of 10 folded articles of the same type before compression, multiplied by 100; i.e., (1-in-Bag Stack Height/stack height before compression)*100, reported as a percentage. The articles before compression may be typically sampled from the production line between the folding unit and the stack packing unit. The method used to measure the In-Bag Stack Height is described in further details in WO2011/041352 (Weisman) with the Universal Diaper Packaging Tester illustrated in FIG. 19 of WO2008/155702A1 (Hundorf).

Test Procedures

The values indicated herein are measured according to the methods indicated herein below, unless specified otherwise. All measurements are performed at 21° C.±2° C. and 50%±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2-05.

Urine Permeability Measurement (UPM) Test Method

This method is used to determine the permeability of a swollen hydrogel layer. The results are generally expressed in UPM units equal to $1\times10^{-7}$ cm$^3$·s/g. The Urine Permeability Measurement Test is disclosed in PCT application WO2012/174026A1, incorporated herein by reference.

Thickness Measurement Method

This method is used to measure the thickness of a component of an article or of the article ("sample") itself in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 4.14 kPa of pressure to the sample.

The caliper gauge is mounted with the lower surface of the contact foot in an horizontal plane so that the lower surface of the contact foot contacts the center of the flat horizontal upper surface of a base plate approximately 20 cm×25 cm. The gauge is set to read zero with the contact foot resting on the base plate.

Ruler: Calibrated metal ruler graduated in mm.

Stopwatch: Accuracy 1 second.

Sample preparation: The sample is conditioned at least 24 hours as indicated above.

Measurement procedure: The sample is laid flat with the bottom side, i.e. the side intended to be placed away from the wearer facing down. The point of measurement (if not otherwise indicated the middle of the sample) is carefully drawn on the top side of the sample, taking care not to compress or deform the sample.

The contact foot of the caliper gauge is raised and the sample is placed flat on the base plate of the caliper gauge with the top side of the sample up so that when lowered, the center of the foot is on the marked measuring point.

The foot is gently lowered onto the sample and released (ensure calibration to "0" prior to the start of the measurement). The caliper value is read to the nearest 0.01 mm, 10 seconds after the foot is released.

The procedure is repeated for each sample. Ten samples are measured in this manner for a given material and the average caliper is calculated and reported with an accuracy of one tenth mm.

Misc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a wearer-facing side and a garment-facing side, and extending in a longitudinal direction and a transversal direction, the article comprising:
    a topsheet on the wearer-facing side;
    a backsheet on the garment-facing side;
    an absorbent core between the topsheet and the backsheet, wherein the absorbent core comprises an absorbent layer in a core wrap, the absorbent layer comprising an absorbent material and having a longitudinally extending central portion, a first side portion disposed transversally outward of the central portion and a second side portion disposed transversally outward of the central portion on another side of the central portion;
    wherein the absorbent core further comprises a first folding guide between the central portion and the first side portion, and a second folding guide between the central portion and the second side portion;
    wherein each side portion comprises a plurality of winglets, each winglet having a proximal side relative to a folding guide and extending outward from this proximal side, and wherein neighboring winglets are separated by a gap between their neighboring sides;

wherein the core wrap comprises a top layer and a bottom layer, and the top layer of the core wrap is bonded to the bottom layer of the core wrap at least through the folding guides and at least some of the gaps between the winglets;

wherein when the absorbent core is folded along the folding guides, the central portion and the side portions form a three-dimensional basin and the gaps between the winglets decrease, the article further comprising:

at least one liquid management layer between the topsheet and the absorbent core wherein the liquid management layer comprises folding guides, each folding guide of the liquid management layer separating a respective side portion of the liquid management layer from a center portion of the liquid management layer, and wherein each of the liquid management layer's side portions comprises a single piece of liquid management material delimited by a distal straight line and a proximal curve to form a crescent shape or a semi-circular shape that superposes a plurality of the winglets.

2. The absorbent article of claim 1, wherein the absorbent core is substantially free of cellulose fibers.

3. The absorbent article of claim 1, further comprising an auxiliary glue between the absorbent layer and at least one of the top layer of the core wrap and the bottom layer of the core wrap.

4. The absorbent article of claim 1, wherein the absorbent material consists essentially of superabsorbent polymer particles and is at least partially immobilized within the core wrap by a microfibrous glue.

5. The absorbent article of claim 1, wherein the folding guides of the absorbent layer are inwardly curved towards the central portion of the absorbent layer.

6. The absorbent article of claim 1, wherein each folding guide of the absorbent layer comprises an extremity and wherein the extremity of each of the folding guides of the absorbent layer extends to a longitudinal side edge of the absorbent layer.

7. The absorbent article of claim 1, wherein for each side portion of the absorbent layer at least one gap has a generally triangular shape.

8. An absorbent article of claim 7, wherein the at least one gap is disposed between two neighboring winglets and the neighboring sides of the two neighboring winglets at their proximal sides form an angle ranging from about 5° to about 60°.

9. The absorbent article of claim 1, wherein each side portion of the absorbent layer comprises from about 3 to about 10 winglets.

10. The absorbent article of claim 1, further comprising a longitudinal axis, a front region, a back region and an intermediate crotch region, each region measuring a third of the length of the article as measured along the longitudinal axis, and wherein the central portion of the absorbent layer extends longitudinally across the front region, crotch region and back region of the article, and the first and second side portions of the absorbent layer are at least partially within the crotch region of the article.

11. The absorbent article of claim 1, further comprising one or more elasticized components, wherein:

the one or more elasticized components are selected from the group of:

a pair of elasticized leg cuffs, each cuff having a proximal edge attached to the topsheet and a free-standing distal edge;

a pair of elasticized gasketing cuffs placed transversally outward from the absorbent layer; and a longitudinally extending elasticized element at least partially placed between the side portions of the absorbent layer and the backsheet; and the one or more elasticized components exerts a contraction force on the absorbent core that brings the absorbent core into a basin shape along the folding guides of the absorbent layer when the article is placed on a wearer.

12. The absorbent article of claim 1, wherein the liquid management layer comprises cross-linked cellulosic fibers.

13. The absorbent article of claim 1, wherein the liquid management layer comprises a resin-bonded nonwoven layer.

14. The absorbent article of claim 1, wherein the liquid management layer comprises a pair of folding guides at least partially superposed with the folding guides of the absorbent core.

15. The absorbent article of claim 1, wherein the folding guides of the absorbent layer each have a length measured in the longitudinal direction which is at least two-tenths of the length of the central portion of the absorbent layer.

16. The absorbent article of claim 1, wherein the length of the folding guides of the absorbent layer is at least about 40 mm as measured in the longitudinal direction.

* * * * *